US008735573B2

(12) United States Patent
Lang et al.

(10) Patent No.: US 8,735,573 B2
(45) Date of Patent: May 27, 2014

(54) METHOD TO RECOVER BIOACTIVE COMPOUNDS

(75) Inventors: Tim Lang, Sydney (AU); Wayne Simpkins, West Pymble (AU)

(73) Assignee: Langtech International Pty Ltd., Sydney, NSW (AU)

( * ) Notice: Subject to any disclaimer, the term of this patent is extended or adjusted under 35 U.S.C. 154(b) by 525 days.

(21) Appl. No.: 12/682,394

(22) PCT Filed: Oct. 9, 2008

(86) PCT No.: PCT/AU2008/001495
§ 371 (c)(1), (2), (4) Date: Jul. 9, 2010

(87) PCT Pub. No.: WO2009/046492
PCT Pub. Date: Apr. 16, 2009

(65) Prior Publication Data

US 2010/0286376 A1 Nov. 11, 2010

(30) Foreign Application Priority Data

Oct. 10, 2007 (AU) ................................ 2007905554

(51) Int. Cl.
*C07H 1/00* (2006.01)
*C07H 1/08* (2006.01)

(52) U.S. Cl.
USPC .......................................................... 536/128

(58) Field of Classification Search
None
See application file for complete search history.

(56) References Cited

U.S. PATENT DOCUMENTS

| | | | | |
|---|---|---|---|---|
| 6,544,581 | B1 | 4/2003 | Shrikhande et al. | |
| 7,238,379 | B2 * | 7/2007 | Lang | 426/542 |
| 2003/0064144 | A1 | 4/2003 | Chu et al. | |
| 2004/0081734 | A1 | 4/2004 | Lang | |

FOREIGN PATENT DOCUMENTS

| | | |
|---|---|---|
| AU | 2001287353 | 3/2002 |
| EP | 0248524 | 12/1987 |
| WO | WO0032062 | 6/2000 |
| WO | WO03074147 | 9/2003 |
| WO | WO2005011836 | 2/2005 |

OTHER PUBLICATIONS

Schoch et al. Journal of Food Science, vol. 67, No. 8, 2002, pp. 3159-3163.*

Kim et al. Journal of Food Engineering 78 (2007) 27-32.*

Scordino et al. J. Agric. Food Chem. 2005, 53, 651-658.*

N. N. Dutta, et.al "Adsorption equilibrium of 7-aminodeacetoxy cephalosporanic acid-cephalexin mixture onto activated carbon and polymeric resins", *Indian Journal of Chemical Technology*, vol. 12, May 2005, pp. 296-303.

Dietmar R. Kammerer et.al "Adsorptive recovery of phenolic compounds from apple juice", *Eur Food Res Technol* (2007) 224: 605-613.

N. N. Dutta, et.al "Aqueous phase adsorption of certain beta-lactam antibiotics onto polymeric resins and activated carbon", *Separation and Purification Technology*, vol. 16, Issue 3, Aug. 9, 1999, pp. 213-224.

Jaclyn L. Brown et. al "Enhanced Hydrogen Bonding for the Adsorptive Recovery and Separations of Oxygenated Aromatic Compounds from Renewable Resources", *Ind. Eng. Chem. Res.*, 2002, 41 (20), pp. 5058-5064.

Marta Otero et.al "Comparative study of the adsorption of phenol and salicylic acid from aqueous solution onto nonionic polymeric resins", *Separation and Purification Technology*, vol. 45, Issue 2, Oct. 2005, pp. 86-95.

M.A. Abdullah et.al "Comparative evaluation of adsorption kinetics and isotherms of a natural product removal by Amberlite polymeric adsorbents", *Chemical Engineering Journal*, vol. 146, Issue 3, Feb. 15, 2009, pp. 370-376.

Aimin Li et.al "Adsorption of phenolic compounds on Amberlite XAD-4 and its acetylated derivative MX-4" *Reactive and Functional Polymers*, vol. 49, Issue 3, Oct. 2001, pp. 225-233.

S.P. Deosarkar et.al "Adsorptive separation and recovery of organics from PHBA and SA plant effluents" *Separation and Purification Technology*, vol. 38, Issue 3, Sep. 2004, pp. 241-254.

E.M. Silva et.al "Optimisation of the adsorption of polyphenols from Inga edulis leaves on macroporous resins using an experimental design methodology" *Separation and Purification Technology*, vol. 53, Issue 3, Mar. 1, 2007, pp. 274-280.

Weiben Yang et. al "Adsorption Mechanism of Aromatic Sulfonates onto Resins with Different Matrices" *Ind. Eng. Chem. Res.*, 2007, 46 (21), pp. 6971-6977.

Jian Gou Huang et.al "Synthesis and Adsorption Property of Two Polymeric Adsorbents with Pendent Ether Bonds" *Chinese Chemical Letters* vol. 14, No. 9, pp. 914-916, 2003; http://www.imm.ac.cn/journal/ccl.html.

Jeffrey A. Koehler et.al "Selective Adsorption of Sterically Hindered Phenols through a Single-Point Binding Mechanism", *Ind. Eng. Chem. Res.*, 1999, 38 (8), pp. 3076-3082.

Jeffrey A. Koehler et.al "Potential Approach for Fractionating Oxygenated Aromatic Compounds from Renewable Resources" *Ind. Eng. Chem. Res.*, 2000, 39 (9), pp. 3347-3355.

* cited by examiner

*Primary Examiner* — Layla Bland

(74) *Attorney, Agent, or Firm* — Cesari and McKenna, LLP

(57) ABSTRACT

The invention relates to a process for separating bioactive compounds obtained from vegetable materials. The invention also relates to a process for extracting bioactive compounds from vegetable material.

24 Claims, 11 Drawing Sheets

METHOD TO RECOVER BIOACTIVE COMPOUNDS

CROSS-REFERENCE TO RELATED APPLICATIONS

This application is the National Stage of International Application No. PCT/AU 2008/001495, filed on Oct. 9, 2008, which claims the priority date of Australian Application No. 2007905554, filed on Oct. 10, 2007 the contents of both being hereby incorporated by reference in their entirety.

FIELD OF THE INVENTION

The present invention relates to a process for separating bioactive compounds obtained from vegetable material. The present invention also relates to a process for extracting bioactive compounds from vegetable material.

BACKGROUND

Plants and vegetable matter contain a range of compounds which are biologically active in humans providing beneficial physiological effects, including a reduction in the risks of cancer, heart disease and arthritis.

A range of bioactive compounds can be found in a wide variety of plant and vegetable material. Citrus fruits for example, contain bioactive compounds that can be included in two major groups; the limonoids and the flavonoids.

The limonoids are triterpenoid compounds which usually occur in citrus fruits. The limonoids may exist as aglycones, or be linked to a glucose molecule (the glucoside). The limonoid glucosides have recently been shown to possess powerful anti-cancer properties in animals.

The flavonoids are a group of benzopyran derivatives which occur widely in plants. The flavonoids typically consist of a benzene ring fused with a heterocyclic six-membered ring containing an oxygen atom. Many flavonoids may also exist as glycosides. In citrus fruits, the most predominant flavonoids are the flavanones, narirutin and hesperidin (in orange) and naringin (in grapefruit). These compounds are capable of lowering blood cholesterol levels in hypercholesterolemic individuals.

The flavonoids in citrus also include the polymethoxylated flavones. This group of compounds is represented by flavones substituted by methoxy groups and is unique to citrus. The polymethoxylated flavones have a wide range of physiological effects, including a very high antioxidant capacity, which has prompted investigations into their potential use as a potent anti-cancer agent and as an anti-inflammatory agent.

Polyphenolic compounds such as the citrus limonoids and citrus flavonoids occur in significantly higher concentrations in peel tissue when compared to the concentration in endocarp from which juice is extracted. The high concentrations of these compounds in the peel tissue help form the basis of the plant's protective mechanisms against bacteria, moulds, yeasts and insects.

Citrus peel is bitter, most often because of the presence of limonoid compounds in their aglycone form, and peel discharged from juicing operations is usually limed, pressed, dehydrated, pelletised and used as stock feed.

Recently, a commercial practice has arisen in the citrus processing industry to extract water soluble compounds from the peel of citrus fruits using a range of devices. The resultant dilute water extract ("juice") is bitter and after clarification (or partial clarification) this juice is de-bittered by passing it over a synthetic polymer adsorbent. In this way, the bitter principles which are adsorbed to the polymer can be separated from the natural sugars and acids and some flavour compounds, which are not adsorbed to the polymer. Most limonoids and flavonoids however may also be preferentially adsorbed by the polymer along with the bitter principles. Treatment of the polymer with a caustic soda solution desorbs these compounds to regenerate the polymer. The treatment however also destroys the bioactive compounds, which are discharged as waste with the spent caustic soda solution.

One process for extracting bioactive components from citrus fruits has been described in PCT/AU01/01113 (WO 02/20112). In this process, a raw citrus extract is passed over a polystyrene-divinyl benzene polymer and bioactive compounds from the raw material are adsorbed onto the polymer. The bioactives are then sequentially eluted from the de-bittering polymer adsorbent by a constant gradient concentration of alcohol in an alcohol water mixture. Three separate alcoholic extracts containing limonoid glucosides, flavanone glycosides and polymethoxylated flavones are then able to be collected from the polymer adsorbent.

While this process enables the valuable bioactive compounds to be recovered from the adsorbent polymer, some mixing of the bioactive compounds in the eluent fractions can occur, leading to incomplete separation of the different bioactives from each other, in particular of the limonoid glucosides from the flavanone glycosides. This may result in a lower purity leading to formulation difficulties, for example.

It would be desirable to address some or all of these problems and to provide an improved process for obtaining bioactive compounds from vegetable material such as citrus fruits.

SUMMARY

The present invention relates in one aspect to a process for the selective separation of bioactive compounds, the process comprising the steps of:

(a) contacting a plurality of bioactive compounds with a polymer adsorbent under conditions allowing adsorption of at least one bioactive compound on to the adsorbent while at least one bioactive compound is not adsorbed on to the adsorbent; and (b) collecting a solution comprising at least one bioactive compound which has not adsorbed onto the adsorbent.

The present invention relates in another aspect to a process for purifying a bioactive compound comprising the step of contacting the bioactive compound with an ion exchange resin under conditions allowing ionic interactions between the bioactive compound and the resin such that the bioactive compound is adsorbed on to the resin.

The present invention also relates in a further aspect to a process for the selective extraction of bioactive compounds from a vegetable material, the process comprising the step of contacting the vegetable material with a solvent under conditions to extract at least one water soluble bioactive compound from the vegetable material to thereby provide an extract comprising the water soluble bioactive compound and a vegetable residue comprising at least one water insoluble bioactive compound.

Yet a further aspect of the present invention provides a bioactive compound produced by a process as described herein.

A further aspect of the invention provides a composition comprising a limonoid glycoside present at a purity of greater than about 10%, 50% or 70%.

DETAILED DESCRIPTION

Figure 1:
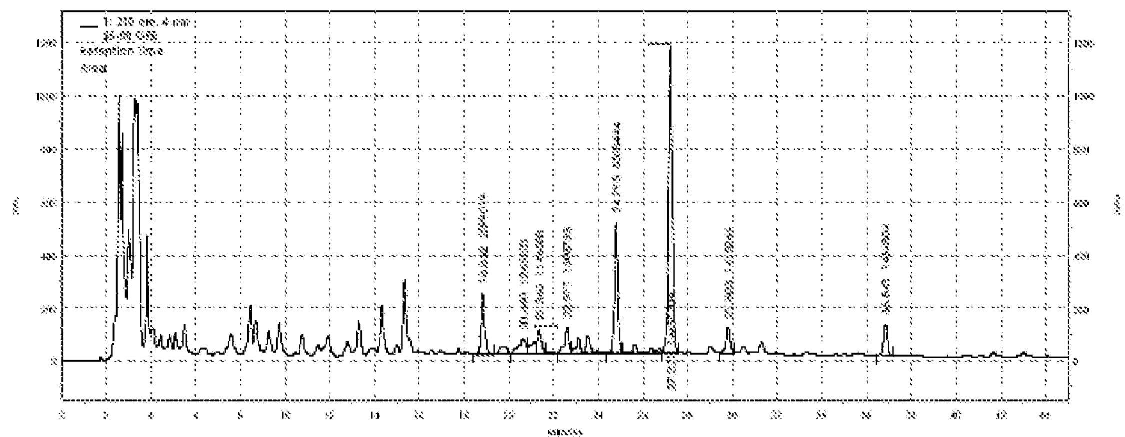
FIG. 1 shows a HPLC chromatogram illustrating the components present in a representative raw extract obtained from orange peel.

The present invention relates in one aspect to a process for separating bioactive compounds. The process of the invention enables bioactive compounds to be selectively separated from one another.

The term "bioactive" as used herein refers to compounds or substances that have an effect upon a living organism, tissue or cell. The person skilled in the art would appreciate that bioactive compounds can be found in many food sources and other naturally occurring substances. In accordance with one embodiment of the invention, the bioactive compounds are obtained from vegetable material.

As used herein, the terms "vegetable matter" and "vegetable material" refer to material derived from plants. A range of bioactive compounds may be found in a wide variety of different vegetable matter or vegetable material. The vegetable material from which the bioactive compounds are obtained may be in any form.

In one embodiment the vegetable material is derived from an edible fruit. Examples of edible fruit include tomatoes, apples, pears, grapes, berries, stone fruit and citrus fruit. Fruits such as grapes may contain a number of bioactive compounds including stilbenes such as resveratrol, flavanols such as quercetin and myricetin, catechins and anthocyanins. Other fruits such as apples may also be a source of bioactive compounds such as catechins, flavanols and dihydrochalcones. In addition, citrus fruits may contain bioactive limonoids, flavonoids and polymethoxylated flavones. Vegetable material derived from edible fruit may be obtained from all the parts of the fruit, including the peel, skin, juice, endocarp, seeds and flesh of the fruit.

In another embodiment the vegetable material is derived from plant material that is not an edible fruit. Such plant material includes the flowers, roots, leaves and stems of a plant. Sugarcane is an example of plant material that is not an edible fruit, which can contain bioactive compounds such as methoxylated flavones and phenolic acids.

In another embodiment the vegetable material is a vegetable extract which is derived from plant material. The vegetable extract is typically a liquid or solution containing essential components which have been recovered from the plant material. An example of a vegetable extract is citrus peel extract which is derived from citrus peel.

While the following detailed discussion of the invention will be largely focussed on bioactive compounds obtained from citrus fruit, it is to be understood that the invention is not so limited and is also applicable to bioactive compounds obtained from other plants and plant material. In particular, the invention may be used to separate bioactive compounds of different physical properties.

In one aspect the present invention provides a process for separating bioactive compounds, the process comprising the step of (a) contacting a plurality of bioactive compounds with a polymer adsorbent under conditions allowing adsorption of at least one bioactive compound on to the adsorbent while at least one bioactive compound is not adsorbed on to the adsorbent. The plurality of bioactive compounds comprises at least two, and preferably comprises more than two bioactive compounds. The plurality of bioactive compounds is preferably provided in a solution, which may be prepared using any technique. In one embodiment, the solution is an extract obtained from vegetable material.

In one embodiment, the vegetable material is derived from a citrus fruit such as oranges, lemons, limes, grapefruits, mandarins, tangerines and the like. All parts of the citrus fruit, including the peel and endocarp of the fruit may provide the vegetable material. Preferably, the vegetable material is derived from the citrus peel. The vegetable material may also be pre-treated in any suitable manner prior to processing in accordance with one aspect of the invention described herein.

A solution comprising a plurality of bioactive compounds may be obtained by contacting the vegetable material with a solvent that extracts the bioactive compounds from the vegetable material. Any suitable solvent may be used. A preferred solvent is water. The extraction of the vegetable material by the solvent may proceed by any suitable process known in the art. For a solution that is an extract derived from citrus fruits, the solution will comprise a mixture of compounds, including limonoid and flavanone bioactive compounds, natural sugars and organic acids. If desired, the solution may be subjected to a pre-treatment step prior to processing in accordance with the invention as described herein. Centrifugation and filtration are examples of pre-treatments that may be used. Such pre-treatment may be desirable to minimise the amount of suspended solids or other undesirable material in the solution.

The plurality of bioactive compounds contacts the polymer adsorbent. The polymer adsorbent has a selective affinity for at least one of the bioactive compounds present in the mixture. As a result, the bioactive compound is substantially adsorbed on to the polymer adsorbent and thereby retained by the adsorbent. The polymer adsorbent furthermore does not have an affinity for at least one other bioactive compound that is present in the mixture of bioactive compounds. Consequently, in accordance with the invention at least one bioactive compound is not adsorbed on to the adsorbent.

Any suitable polymer adsorbent that is capable of selectively adsorbing at least one bioactive compound may be used. Without wishing to be limited by theory, it is believed that favourable interactions, such as ionic or hydrogen bonding interactions enhance the ability of a given bioactive compound to be adsorbed on to the polymer adsorbent. In one embodiment, the polymer adsorbent is an acrylic. In one embodiment, a suitable polymer adsorbent is an acrylic ester.

One example of an acrylic ester is polymethylmethacrylate. The polymethylmethacrylate may be crosslinked with a suitable crosslinking agent such as ethylene glycol. It is preferred that the polymer adsorbent be non-ionic. An example of a polymer adsorbent suitable for use in the invention is Alimentech P495 Inert Adsorbent Polymer supplied by Bucher Foodtech.

The polymer adsorbent may be provided in any suitable form and arrangement. In one embodiment, the polymer adsorbent is an acrylic that is provided in the form of beads. The beads may be of any suitable shape or size. The polymer adsorbent may be arranged in any suitable manner. In a preferred embodiment, the polymer adsorbent is arranged in the passage, which may be a column, container, vessel or pipe. Gravity fed columns and flash chromatography columns are examples of suitable arrangements. Other arrangements, such as moving bed chromatography apparatus, may also be used. The ratio of the length of the column to its diameter is at least 4:1, and preferably at least 8:1. The passage may contain any suitable volume of the adsorbent.

In one embodiment, a solution comprising the plurality of bioactive compounds is applied to the top of a vertically arranged column containing an acrylic polymer adsorbent. While embodiments of the invention are described herein with reference to the application of various solutions to the top of a vertically arranged column, the person skilled in the art would appreciate that other arrangements, and other means of introducing solutions to the arrangements, may also be used. For example, solutions may be fed into the bottom of a vertically arranged column. Alternatively, if a column is arranged in a substantially horizontal manner, the solutions may be fed into one end of the horizontal column.

The solution is then allowed to percolate through the adsorbent. Any quantity of solution may be applied to the absorbent and a person skilled in the relevant art would appreciate that the amount of solution may depend on the size of the column as well as the type of adsorbent used. The solution is allowed to pass through the passage at any rate that enables the solution to sufficiently contact the adsorbent. A person skilled in the art would understand that a suitable rate would depend on a number of factors, including the size of the apparatus and whether the process is carried out at a laboratory or industrial scale.

As the solution comprising the plurality of bioactive compounds passes through the column containing the polymer adsorbent, at least one bioactive compound is substantially adsorbed on to the polymer adsorbent. The retention of the at least one bioactive compound by the adsorbent removes the compound from the solution.

After the solution has passed through the column, it leaves the column and is collected. At least one bioactive compound present in the solution, which has not been adsorbed on to the polymer adsorbent, also leaves the column with the solution. The solution that elutes through and leaves the column is also known as an eluate. Thus the process of the invention also comprises the step of (b) collecting a solution comprising the at least one bioactive compound which has not adsorbed on to the adsorbent. The at least one bioactive compound which has not adsorbed on to the adsorbent may be collected in a single solution fraction of eluate or in multiple fractions. Other components that have not been adsorbed on to the polymer adsorbent may also be present in the collected fractions. The collected solution (eluate) may be analysed for the presence of a bioactive compound by any suitable method. A preferred method involves the use of high performance liquid chromatography (HPLC). As will be described below, the eluted bioactive compound may undergo additional treatment to further purify the bioactive compound.

In one embodiment, where the plurality of bioactive compounds contains a mixture of flavonoid and limonoid bioactive compounds, the polymer adsorbent is one that is capable of separating the flavonoid and limonoid compounds. Preferably, the polymer adsorbent is an acrylic, more preferably an acrylic ester and even more preferably polymethylmethacrylate. An acrylic polymer adsorbent has been found to selectively bind the bioactive flavanones and their derivatives, such as the flavanone glycosides, more strongly than to limonoid compounds, such as the limonoid glucosides. This selective adsorption allows the flavanones to be substantially retained by the adsorbent while the limonoid glucoside compounds are not retained by the adsorbent. In this manner, the two groups of bioactive compounds are substantially separated. In one form of the method, the two groups of bioactive compounds are completely separated. Other compounds such as natural sugars and organic acids also are not retained by the adsorbent. Thus where the acrylic adsorbent is arranged in a column, the natural sugars and organic acids rapidly pass through the column ahead of the limonoid glucosides while the flavonoid compounds do not pass through. Thus in accordance with one aspect of the invention a flavanone glycoside may be substantially separated from a limonoid glucoside.

In another embodiment, the plurality of bioactive compounds may also contain other bioactive compounds such as the polymethoxylated flavones and limonoid aglycones in addition to the flavonoid compounds and limonoid glucosides. In this embodiment, the polymer adsorbent is capable of adsorbing polymethoxylated flavones and limonoid aglycones along with the flavonoid compounds. The method of the invention therefore also enables these compounds to be substantially separated from the limonoid glucosides and small molecule polar constituents such as naturally occurring sugars and organic acids.

In accordance with the one aspect of the invention, the process may comprise the steps of (c) contacting the at least one bioactive compound adsorbed on the polymer adsorbent of step (a) with an eluent under conditions allowing desorption of the at least one bioactive compound from the adsorbent, and (d) eluting the at least one bioactive compound from the adsorbent.

When the polymer adsorbent is arranged in a passage such as a column, the eluent is typically introduced in aliquots or as a continuous stream at the top of the column and allowed to percolate through the adsorbent. Where aliquots are introduced, one or more aliquots of eluent may be employed. The eluent acts to desorb the at least one bioactive compound from the adsorbent and to carry the bioactive compound through the column. The eluent is preferably fed to the passage at a pre-determined rate, which may vary between 1 and 5 bed volumes per hour and preferably, is between 1 to 2 bed volumes per hour.

The eluent may comprise any suitable solvent or mixture of solvents. Preferably, the solvent or mixture of solvents is selected from those permitted for use in food grade products. A preferred solvent is a water soluble solvent. In one embodiment, the eluent comprises alcohol and water.

Where the eluent comprises alcohol, any concentration of alcohol may be used. In one embodiment, the concentration of alcohol in the eluent is in the range of between about 10 to 80% (v/v). A person skilled in the art would understand however that the concentration of alcohol used may vary depending on the nature of the bioactive compound and the desired result. In addition, any suitable alcohol may be employed in the eluent. In one embodiment the alcohol is ethanol.

In one embodiment, the concentration of alcohol in the eluent remains substantially constant during desorption of the at least one bioactive compound from the adsorbent. A preferred alcohol concentration is about 40% (v/v). In another embodiment, the concentration of alcohol in the eluent increases during desorption of the at least one bioactive compound from the adsorbent. Preferably, the alcohol concentration increases from about 20% to about 80% (v/v). The concentration of alcohol may increase at a substantially constant rate or it may increase in a step-wise manner. Where the eluent provides a gradient concentration of alcohol, aliquots of eluent containing increasing alcohol contents can be sequentially introduced to the top of the column.

Upon leaving the column, the resulting eluate may then be collected in fractions. At least one fraction, and preferably multiple fractions, corresponding to the presence of the desorbed bioactive compounds are collected.

It is emphasised that while fractional collection methods may be useful in some embodiments of the method, non-fractional collection methods are included in the scope of the present invention. For example, a target bioactive compound may be allowed to adsorb to the polymer adsorbent, while contaminant molecules are allowed to simply pass through the column to waste. After substantially all contaminant molecules are removed from the polymer adsorbent matrix (for example by washing the matrix with a solution that does not desorb the target bioactive compound), the target bioactive compound may be desorbed by the application of an appropriate solution, and the bulk collection of target compound collected in a single volume.

Fractions or bulk collected volumes may be analysed to determine the presence or amount of bioactive compounds. A preferred analysis method involves the use of High Performance Liquid Chromatography (HPLC). In one embodiment, where flavanones and their derivatives have adsorbed on to the polymer adsorbent, the collected fraction therefore contains the desorbed flavonoid compounds.

Where polymethoxylated flavones and limonoid aglycones have also been adsorbed on to the polymer adsorbent in addition to the bioactive flavonoid compounds, the eluent used to remove the flavonoid compounds may not desorb the polymethoxylated flavones and limonoid aglycones from the adsorbent. Accordingly, the polymethoxylated flavones and limonoid aglycones may remain bound to the polymer adsorbent during desorption of the flavonoid compounds. Thus, in accordance with another aspect of the invention a flavonoid compound may be substantially separated from a polymethoxylated flavone and/or a limonoid aglycone.

If desired, after desorption of the flavonoid compounds, the polymer adsorbent may be washed with a suitable solution to remove any adsorbed polymethoxylated flavones and limonoid aglycones from the polymer adsorbent to re-generate the polymer adsorbent for further use. Any suitable solution may be used to remove the adsorbed polymethoxylated flavones and limonoid aglycones from the polymer adsorbent. An example of a solution that can be used to desorb the polymethoxylated flavones and limonoid aglycones is 0.5M sodium hydroxide.

In a further aspect of the invention, the bioactive compound that has not adsorbed on to the polymer adsorbent may be further purified. In accordance with this aspect of the invention, the process may comprise the step of (e) contacting the solution comprising the at least one bioactive compound obtained from step (b) with a polymer adsorbent under conditions allowing adsorption of the at least one bioactive compound on to the adsorbent, and (f) collecting the solution eluted from the polymer adsorbent.

Unlike the polymer adsorbent used previously, the polymer adsorbent employed in step (e) is selected from any of those that have the ability to bind to the bioactive compound present in the solution. Preferably, the polymer adsorbent is capable of adsorbing non-polar compounds. A preferred polymer adsorbent is polystyrene-divinyl benzene. Polar components such as natural sugars and simple organic acids that may also be present in the solution are not adsorbed by the polymer adsorbent and are carried with the solution as it leaves the polymer adsorbent and is eluted. An example of a commercially available polystyrene-divinyl benzene polymer adsorbent is Amberlite XAD-16 manufactured by Rohm and Haas.

The polymer adsorbent employed in step (e) may be provided in any suitable form and arrangement. In one embodiment, the polymer adsorbent is a polystyrene-divinyl benzene polymer in the form of beads. The beads may be of any suitable shape or size. The beads may be arranged in any suitable manner. The beads are preferably arranged in the passage, which may be provided by packing the beads in a column, container, vessel or pipe. The passage may contain any suitable volume of the beads. In one preferred embodiment of the invention, the bed volume of the polymer adsorbent used in step (e) is equivalent that the bed volume of the polymer adsorbent used in step (a) above. For example, where the bed volume of the polymer adsorbent used in step (a) is at least about 250 litres, the bed volume of the polymer adsorbent employed in step (e) may also be at least about 250 litres. However, a person skilled in the relevant art will understand that the volume of polymer adsorbent used in step (e) may be varied depending on the nature of the bioactive compounds and the desired result.

In one embodiment, the solution obtained from step (b), which comprises the at least one bioactive compound, is applied to the top of a column containing the polymer adsorbent and allowed to percolate through the adsorbent in order to contact the polymer adsorbent in step (e). In one embodiment, when the solution comprises bioactive limonoid compounds and derivatives such as limonoid glucosides, the limonoids bind to the polymer adsorbent during passage of the solution through the adsorbent and are thereby removed from the solution. The solution traverses the passage and upon leaving the passage and polymer adsorbent, is collected as an eluate. In one embodiment, where the collected solution (or eluate) contains sugars and simple organic acids, the eluted solution may be regarded as a purified “juice” component. It has been found that the juice obtained in accordance with the process of the invention is neutral and not bitter. It is contemplated that the purified “juice” component may be isolated and, if desired, further treated for use as a supplement in food products such as beverages.

In accordance with one embodiment of the invention, once the solution has eluted from the adsorbent, the at least one bioactive compound may be desorbed from the polymer adsorbent of step (e). Accordingly, the present invention may further comprise the step of (g) contacting the at least one bioactive compound adsorbed on the polymer adsorbent employed in step (e) with an eluent under conditions allowing desorption of the at least one bioactive compound from the adsorbent, and (h) eluting the at least one bioactive compound from the adsorbent. One or more aliquots of eluent, or a continuous stream of eluent, may be used to desorb the at least one bioactive compound from the polymer adsorbent.

Similar to the eluent used to desorb bioactive compounds from the polymer adsorbent in step (c) as described above, the eluent employed in step (g) may comprise any suitable solvent or mixture of solvents. Preferably, the solvent or mixture of solvents is selected from those permitted for use with food products. In one embodiment, the eluent comprises alcohol and water. Where the eluent comprises alcohol, any suitable concentration of alcohol may be used. In one embodiment, the concentration of alcohol in the eluent is in the range of from about 10 to 80% (v/v). A person skilled in the art would understand however that the concentration of alcohol used may vary depending on the nature of the bioactive compound and the desired result. In addition, any type of alcohol may be used. A preferred alcohol is ethanol.

In one embodiment, the concentration of alcohol in the eluent remains substantially constant during desorption of the at least one bioactive compound from the adsorbent. Preferably, the eluent comprises about 40% (v/v) alcohol. In another embodiment, the concentration of alcohol in the eluent increases during desorption of the at least one bioactive compound from the adsorbent. Preferably, the alcohol concentration increases from about 10% to about 80% (v/v). The concentration of alcohol may increase at a substantially constant rate or it may increase in a step-wise manner. Where the eluent provides a gradient concentration of alcohol, aliquots of eluent containing increasing alcohol contents can be sequentially introduced to the top of a column containing the polymer adsorbent.

The bioactive compound eluted from the polymer adsorbent in accordance with step (h) is typically collected in an eluate fraction. The eluate fraction is a solution that comprises the bioactive compound together with the solvent used to elute the bioactive compound from the polymer adsorbent. At least one fraction, and preferably a plurality of eluted fractions, corresponding to the presence of the bioactive compound are collected. In one preferred embodiment of the invention, the collected eluate fraction contains limonoid compounds such as limonoid glucosides. Where more than one eluate fraction is collected, the eluate fractions may be combined to form a single fraction. In addition, as discussed above, non-fractional collection methods which enable the target bioactive molecule to be collected in a single bulk volume may also be used if desired.

In the case of the limonoids, the use of an eluent in which the concentration of alcohol increases during desorption of the limonoids may be advantageous where it is desired to separate selected limonoid compounds from each other. Different limonoid compounds possess different polarities due to differences in chemical structure. Accordingly, the use of an alcohol gradient may assist to separate the limonoid compounds based on differences in polarity. In terms of order of elution as the concentration of alcohol in the eluent increases, limonin glucoside, which is the most polar compound, is eluted first from the polymer adsorbent, followed by nomilin glucoside, nomilinic acid glucoside and obacunone glucoside. A person skilled in the relevant art would be able to adjust the alcohol concentration in the eluent and determine whether the desired separation is achieved by monitoring the elution of the limonoid compounds using analytical methods such as HPLC.

In some embodiments of the invention, the bioactive compounds that are eluted from the polymer adsorbent may be further treated to purify and concentrate the bioactive compounds.

In another aspect, the present invention relates to a process for purifying a bioactive compound, the process comprising the step of contacting the bioactive compound with an ion exchange resin under conditions allowing ionic interactions between the bioactive compound and the resin such that the bioactive compound is adsorbed on to the resin.

Where at least one bioactive compound has been eluted from a polymer adsorbent in accordance with the process of one aspect of the invention, the process may further comprise the step of contacting the eluted bioactive compound with an ion exchange resin under conditions allowing ionic interactions between the at least one bioactive compound and the resin such that the at least one bioactive compound is adsorbed on to the resin.

In one embodiment, the bioactive compound to be purified is a bioactive obtained after elution from a polymer adsorbent, in accordance with step (h) described above. In this embodiment, the bioactive compound is typically provided in a solution with the elution solvent. It is an advantage of the present invention that the solution (or eluate) comprising the bioactive compound can be directly applied to the ion exchange resin without the need to remove excess alcohol from the solution by evaporative or other processes prior to exposure of the bioactive compound to the ion exchange resin.

In one embodiment the ion exchange resin is an anionic exchange resin and preferably, is a weak anion exchange resin. An example of a weak anion exchange resin that may be used in the present invention is the Diaion WA-30 resin supplied by Supelco.

The ion exchange resin may be provided in any suitable form and arrangement. A range of suitable forms and arrangements would be apparent to a person skilled in the relevant art. The resin may be arranged in the passage, which may be provided by packing the resin in a column such as a gravity fed column or a flash chromatography column. The passage may contain any suitable volume of the resin. In one embodiment, the bed volume of the ion exchange resin is about 20% of the bed volume of polymer adsorbent used in step (a) above. For example, if 100 litres of polymer adsorbent is used in step (a), then 20 litres of ion-exchange resin may only be required. A person skilled in the art will however, understand that the required volume of ion exchange resin may vary depending on the nature of the bioactive compounds and the desired result.

In one embodiment, a solution containing the bioactive compound is introduced to the top of the resin contained in a column and allowed to percolate through the resin. In this manner, contact between the bioactive compound and the ion exchange resin is achieved.

It is believed that ionic interactions between the resin and bioactive compounds such as the limonoid glucosides lead to the selective adsorption of the bioactive compounds on to the resin. Other components that may be present that are unable to participate in the ionic interactions will not bind to the resin. Accordingly, the bioactive compounds may be concentrated and further separated from any undesirable components which may contaminate the bioactive compounds.

Bioactive compounds that have adsorbed on to the ion exchange resin may be recovered by contacting the ion exchange resin with a solution comprising a suitable solute under conditions allowing displacement of the bioactive compound from the resin. The solute may be selected from any of those that are able to compete with the bioactive compound for binding sites in the ion exchange resin. A preferred solute is a salt, such as sodium chloride. The solute may be present in any suitable concentration. In one embodiment, the solution is a 0.5M sodium chloride solution.

In one embodiment, where the bioactive compound is a limonoid glucoside, a solute solution comprising a salt as the solute may be passed through a passage containing the ion exchange resin. One or more aliquots of the solute solution, or a continuous stream of the solute solution, may be introduced to the passage containing the ion exchange resin. The salt competitively binds to the resin and displaces the limonoid glucoside from the resin. The desorbed limonoid glucosides are subsequently collected as volumes of the solute solution leaves the passage. The desorbed limonoid glucosides may be collected in a single fraction or multiple fractions, or in a bulk volume of the eluted solute solution.

After collection of the bioactive compound, any solute that is present in the collected fractions is preferably removed. The solute may be removed by any suitable process. In a preferred embodiment, the solute is removed by contacting the fractions with a polymer adsorbent. The fractions are contacted with the adsorbent under conditions allowing adsorption of the bioactive compound on to the adsorbent.

Any suitable polymer adsorbent may be used. Preferably, the polymer adsorbent is capable of adsorbing non-polar compounds. A preferred polymer adsorbent is polystyrene-divinyl benzene. An example of a suitable polystyrene-divinyl benzene polymer adsorbent is Amberlite XAD-16 manufactured by Rohm and Haas. Similar to the polymer adsorbents described above, the adsorbent may be provided as beads in a passage such as a column. Any suitable volume of the polymer adsorbent may be used. In one embodiment, the bed volume of the polystyrene-divinyl benzene polymer resin may be about 20% of the bed volume of polymer adsorbent used in step (a) above. A person skilled in the art however will understand that the required volume of polymer resin may vary depending on the nature of the bioactive compounds and the desired result.

In one embodiment, a collected volume of solute solution comprising the bioactive compound is applied to the top of the column and allowed to percolate through the adsorbent. Where the bioactive compound comprises limonoid compounds, the limonoids bind to the polymer adsorbent and are substantially retained by the polymer adsorbent. Meanwhile, the solute does not bind to the adsorbent and is eluted from the adsorbent. In this manner, the limonoid bioactive compounds are separated from the undesirable solute.

The bioactive compound may then be desorbed from the polymer adsorbent by contacting the polymer adsorbent with an eluent and eluting the bioactive compound from the adsorbent in accordance with previously described procedures. A preferred eluent comprises a mixture of alcohol and water. Any suitable concentration of alcohol may be used. In one embodiment, the eluent comprises alcohol in an amount in the range from about 10 to about 80% (v/v). In addition, any suitable alcohol may be used. A preferred alcohol is ethanol.

The concentration of alcohol in the eluent may remain substantially constant. In a preferred embodiment, the eluent comprises at least about 40% (v/v) alcohol and more preferably, comprises about 70% (v/v) alcohol. Alternatively, the concentration of alcohol may increase during desorption of at least one bioactive compound from the adsorbent. Where the concentration of alcohol increases during desorption of the bioactive compound, the alcohol content may increase at a substantially constant rate or in a step-wise manner. In one embodiment, the concentration of alcohol in the eluent may increase from about 10 to 80% (v/v) during desorption of at least one bioactive compound from the adsorbent.

The eluted bioactive compound is subsequently collected in at least one, and preferably in multiple fractions corresponding to the presence of the bioactive compound. The presence of the bioactive compound may be analysed by any suitable method. An example of a suitable method is HPLC.

The obtained bioactive compound has been found to be of higher purity than bioactives prepared using prior art processes.

In another aspect, the present invention relates to a purified bioactive compound prepared by a process as described herein. In one embodiment, the bioactive compound is a limonoid compound, more preferably a limonoid glucoside. In another embodiment, the purified bioactive compound is a flavonoid compound, preferably a flavonone glycoside.

In yet another aspect, the present invention relates to a process for the selective extraction of bioactive compounds from a vegetable material, the process comprising the step of contacting the vegetable material with a solvent under conditions allowing extraction of at least one water soluble bioactive compound from the vegetable material to thereby provide an extract comprising the water soluble bioactive compound and a vegetable residue comprising the at least one water insoluble bioactive compound. In a preferred embodiment, the solvent used to contact the vegetable material is water. Accordingly in this embodiment, an aqueous extract containing the at least one water soluble bioactive compound is formed.

The term "vegetable material" is used herein to refer to material derived from plants. The vegetable material may be in any form as described herein. The vegetable material may also be pre-treated in any suitable manner prior to processing in accordance with the invention as described herein. In one embodiment the vegetable material may be derived from an edible fruit, such as those described herein. The vegetable material may be derived from a citrus fruit such as oranges, lemons, limes, grapefruits, mandarins, tangerines and the like. All parts of the citrus fruit, including the peel and endocarp of the fruit may provide the vegetable material. In one embodiment, the vegetable material may be derived from the citrus peel. The vegetable material may also be a vegetable extract derived from plant material.

The solvent may contact the vegetable material using any suitable technique. In one embodiment, a counter-current extractor is used to contact the solvent with the vegetable material and thereby extract the at least one water soluble bioactive compound from the vegetable material. In another embodiment, the vegetable material is treated in manner that results in the vegetable material being placed in a finely divided form. The digested vegetable material is then run through a roller to squeeze out juices containing water soluble bioactive compounds. In one embodiment, the vegetable material comprises limonoids such as limonoid glucosides and flavonoid compounds such as flavanone glycosides as water soluble bioactive compounds.

The extraction of the water soluble bioactive materials from the vegetable material may be performed under any suitable conditions. In one embodiment, the vegetable material is treated at a temperature of at least 70° C., typically for a short period. In one embodiment of the method, the vegetable material is treated at a temperature of at least 70° C. for about 2 minutes. Without wishing to be limited by theory, it is thought that the high temperature treatment step assists to destroy oxidative enzymes and microbes, which may be detrimental to the desired end product. The high temperature may also assist in the disruption of the cellular structure of the vegetable material, enabling soluble compounds in the vegetable material to diffuse into the counter-flowing solvent. Following this, the temperature of the vegetable material may then be lowered to optimize the extraction of the desirable compounds.

After extraction of the water soluble bioactive compounds from the vegetable material, a vegetable residue remains. The vegetable residue may comprise at least one water insoluble bioactive compound, which is not removed by the initial solvent extraction procedure. The vegetable residue may be in the form of a solid or a liquid, depending on the initial form of the vegetable material.

In another aspect of the invention, the resulting vegetable residue may be contacted with an extraction solution comprising alcohol in order to extract at least one water insoluble bioactive compounds from the vegetable residue. The solution may contact the vegetable residue for any time and under any conditions sufficient to extract at least one water insoluble bioactive compound from the residue and thereby provide an alcoholic extract comprising the at least one water insoluble bioactive compound. In one embodiment, the vegetable material and hence the vegetable residue comprises polymethoxylated flavones as the water insoluble bioactive compounds.

Any suitable technique may be used to contact the extraction solution with the vegetable residue and thereby extract at least one water insoluble bioactive compound from the residue. In one preferred embodiment, a counter-current extractor is used.

The extraction solution that contacts the vegetable residue may comprise any suitable amount of alcohol. In one embodiment, the extraction solution comprises a mixture of water and alcohol. Preferably, the extraction solution comprises at least about 10% alcohol and more preferably at least about 20% alcohol. Any suitable alcohol may be used. A preferred alcohol is ethanol.

If required, the alcoholic extract containing the at least one water insoluble bioactive compound may be subsequently contacted with a polymer adsorbent under conditions allowing adsorption of the water insoluble bioactive compound on to the adsorbent. This assists to further purify the water insoluble bioactive compounds by separating the water insoluble bioactive compounds from any impurities that are not able to be retained by the adsorbent. The polymer adsorbent is preferably one that adsorbs to non-polar compounds. A preferred polymer adsorbent is polystyrene-divinyl benzene. An example of a suitable polystyrene-divinyl benzene polymer adsorbent is Amberlite XAD-16 manufactured by Rohm and Haas.

The polymer adsorbent may be provided in any suitable form and arrangement. In one embodiment, the polymer adsorbent is a polystyrene-divinyl benzene polymer in the form of beads. The beads may be of any suitable shape or size. The beads may be arranged in the passage, which may be provided by packing the beads in a column, container, vessel or pipe. Gravity fed columns and flash chromatography columns are examples of suitable columns. The passage may contain any suitable volume of the beads. A person skilled in the art would understand that the volume of polymer adsorbent used may depend upon a number of factors, such as for example, the amount of material to be applied to the adsorbent. Other arrangements, such a moving bed chromatography apparatus, may also be used.

In one embodiment, the alcoholic extract comprising the at least one water insoluble bioactive compound is introduced to the top of a column comprising the adsorbent and allowed to percolate through the adsorbent. In this manner, the at least one water insoluble bioactive compound are able to contact the polymer adsorbent. The water insoluble bioactive compound, being generally non-polar in nature, is retained by the adsorbent while polar components that may be present in the extract are not retained and pass through the passage and are collected. In one embodiment the at least one water insoluble bioactive compound comprises polymethoxylated flavones. Thus, the polymethoxylated flavones are adsorbed on to the polymer adsorbent.

Water insoluble bioactive compounds may be subsequently removed from the adsorbent by contacting the adsorbent with an eluent under conditions allowing desorption of the water insoluble bioactive compounds from the adsorbent, and eluting the water insoluble bioactive compounds from the adsorbent.

Where the polymer adsorbent is arranged in a column, the eluent may be introduced in aliquots, or in a continuous stream, at the top of the column and allowed to percolate through the adsorbent. Where the eluent provides a gradient concentration of alcohol, aliquots of eluent containing increasing alcohol contents can be sequentially introduced to the top of the column. The eluent acts to desorb the bioactive compounds from the adsorbent and carry the bioactive compounds through the column. The eluent is preferably fed to the passage at a pre-determined rate, which may vary between 1 and 5 bed volumes per hour. A person skilled in the art would understand however, that a suitable rate would depend on number of factors, including the size of the apparatus and whether the process is carried out at a laboratory or industrial scale.

The eluent may comprise any suitable solvent or mixture of solvents. Preferably, the solvent or mixture of solvents is selected from those permitted for use in food products. In one embodiment, the eluent comprises alcohol and water. Where the eluent comprises alcohol, any concentration of alcohol may be used. Preferred alcohol concentrations are in the range of from about 10 to 80% (v/v). However, it would be appreciated by the skilled addressee that the concentration of alcohol used may vary depending on the nature of the bioactive compound and the desired result. In addition, any suitable alcohol may be employed in the eluent. A preferred alcohol is ethanol.

The concentration of alcohol in the eluent may remain substantially constant. In a preferred embodiment, the eluent comprises at least about 40% (v/v) alcohol, preferably at least about 50% alcohol and more preferably, about 70% (v/v) alcohol. Alternatively, the concentration of alcohol may increase during desorption of the at least one bioactive compound from the adsorbent. The alcohol content may increase at a substantially constant rate or in a step-wise manner. In one embodiment, the concentration of alcohol in the eluent may increase from about 10 to 80% (v/v) during desorption of at least one bioactive compound from the adsorbent.

Upon leaving the column, the eluent is then collected. At least one fraction, and preferably multiple fractions, of eluent corresponding to the presence of the desorbed water insoluble bioactive compounds are collected. Furthermore, non-fractional collection methods may also be employed. The collected solution may be analysed to determine the presence of bioactive compounds. A preferred analysis method involves the use of HPLC.

In one embodiment the water insoluble bioactive compounds derived from the vegetable material and the vegetable residue comprises polymethoxylated flavones. In one embodiment therefore, the fraction collected from the polymer adsorbent contains the desorbed polymethoxylated flavone compounds. The polymethoxylated flavones have been separated from other bioactive compounds present in the vegetable material.

In a further aspect, the present invention relates to purified polymethoxylated flavones prepared by a process as described herein.

Figure 20:
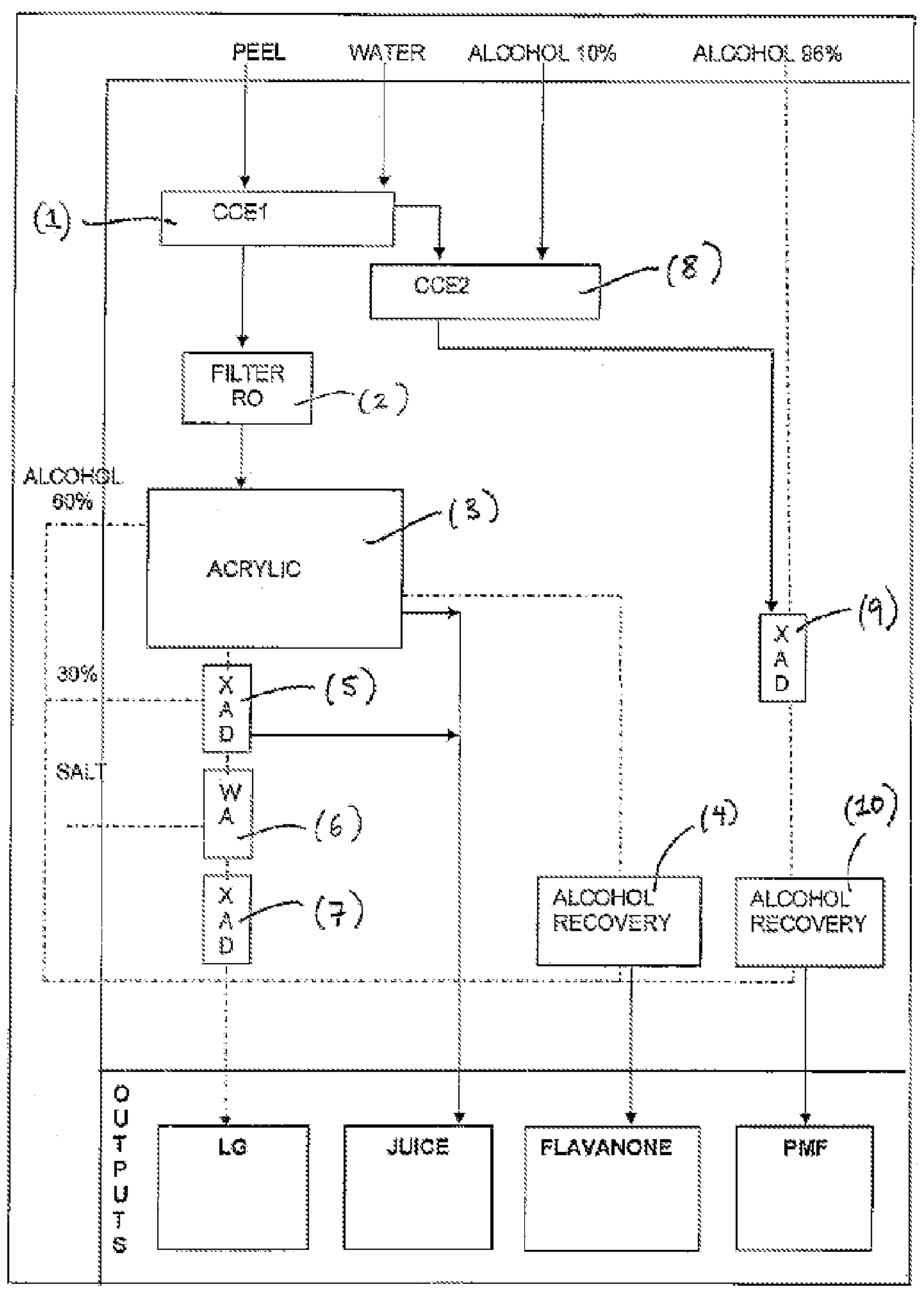
FIG. 20 is a schematic diagram illustrating a system for carrying out a process for selectively separating bioactive compounds in accordance with one embodiment of the invention.

Referring now to FIG. 20, a schematic diagram of a system for carrying out a process in accordance with one embodiment of the invention is shown. In this embodiment, a vegetable extract obtained from citrus peel is fed into a counter current extractor (1) and contacted with water to extract water-soluble components from the citrus peel extract. The water soluble components, which include bioactive flavonoid and limonoid compounds, are isolated in an aqueous extract. The aqueous extract is then fed to a filter (2) to remove any solid material from the extract. The filtered aqueous extract is loaded onto a column packed with an acrylic polymer adsorbent (3). The flavonoid compounds are adsorbed onto the acrylic adsorbent (3) while the limonoid compounds, which do not substantially adhere to the acrylic adsorbent (3), pass through the adsorbent (3) and are collected.

The adsorbed flavonoid compounds are desorbed from the acrylic adsorbent (3) by passing an eluent containing 60% ethanol in water through the column (3). Eluate fractions corresponding to the desorbed flavonoid compounds are then collected. The collected fractions are passed on to alcohol recovery evaporators (4) which remove most of the ethanol to allow collection of the purified flavonoid compounds. The removed ethanol can be stored in an ethanol tank and subsequently distilled for re-use if desired.

A solution containing the limonoid compounds which have eluted from the acrylic polymer adsorbent (3) is then loaded onto a column packed with a polystyrene-divinyl benzene polymer adsorbent (5). The limonoid compounds (and possibly some other non-polar compounds such as flavonoids) are adsorbed onto the polystyrene-divinyl benzene adsorbent (5) while polar components such as the natural sugars and simple organic acids are not adsorbed and are eluted from the polymer adsorbent (5). The eluted solution, which contains the natural sugars and simple organic acids, forms a purified "juice" component and is subsequently collected. An eluent comprising 30% ethanol in water is then used to remove the adsorbed limonoid compounds from the polystyrene-divinyl benzene polymer adsorbent (5) and fractions corresponding to the presence of the desorbed limonoid compounds are collected.

After desorption from the polystyrene-divinyl benzene polymer adsorbent (5), the fractions containing the limonoid compounds are then loaded onto a column containing an anion exchange resin (6). The anion exchange resin (6) adsorbs the limonoid compounds while any components that do not bind to the anion exchange resin pass through the column containing resin (6) and are collected. A salt solution is then loaded onto the anion exchange resin (6) to desorb the limonoid compounds from the resin (6). Fractions containing the desorbed limonoid compounds as well as the salt are collected. The collected fractions correspond to the presence of the limonoid compounds.

The fractions containing the limonoid compounds desorbed from the anion exchange resin (6) are then subsequently loaded onto a column containing a polystyrene-divinyl benzene polymer adsorbent (7). The polymer adsorbent (7) is used to remove the salt present in the solution with the limonoid compounds. The limonoid compounds adsorb on to the polystyrene-divinyl benzene polymer adsorbent (7) while the salt, which is not adsorbed, passes through the column containing the polymer adsorbent (7). The limonoid compounds are then desorbed from the polymer adsorbent (7) by passing an alcoholic solution through the adsorbent (7). Eluate fractions corresponding to the presence of the desorbed limonoid compounds are then subsequently collected.

The collected fractions comprising the desorbed limonoid compounds may be passed on to alcohol recovery evaporators (4) to remove the ethanol from the fractions and allow collection of the purified limonoid compounds. The removed ethanol can be stored in an ethanol tank and subsequently distilled for re-use if desired.

After extraction of the water soluble components, the citrus peel extract can be further extracted by feeding the citrus peel extract to a second counter-current extractor (8) and contacting with a 10% aqueous ethanol solution in order to extract water-insoluble compounds from the peel extract. This process provides an alcoholic extract comprising water-insoluble compounds, including polymethoxylated flavone bioactive compounds.

The alcoholic extract is loaded onto a column containing a polystyrene-divinyl benzene polymer adsorbent (9). Non-polar water insoluble compounds such as the polymethoxylated flavones adsorb onto the polystyrene-divinyl benzene adsorbent (9) and are retained by the adsorbent while any components that are not able to adsorb onto the polymer adsorbent pass through the adsorbent (9).

The adsorbed polymethoxylated flavones are subsequently removed from the polystyrene-divinyl benzene adsorbent (9) by passing a 96% ethanol and water solution through the column. The desorbed polymethoxylated flavone compounds are then collected in eluate fractions corresponding to the presence of the bioactive compounds. The collected eluate fractions may be passed on to alcohol recovery evaporators (10) which remove the ethanol to allow collection of the purified polymethoxylated flavones. If desired, the removed ethanol can be stored in an ethanol tank and subsequently distilled for re-use.

The above system may be operated as a continuous process or in a batch-wise manner. In a continuous process, columns containing each of the required polymer adsorbents and the anion exchange resin may be arranged in a sequence, such that once the desired bioactive compounds are eluted from one column, the resultant eluate is directly fed onto the subsequent column.

The bioactive compounds obtained in accordance with the present invention may also be treated in any suitable manner that facilitates the subsequent use or storage of the compounds. In one preferred embodiment, the bioactive compounds may be subjected to evaporative processes, such as for example freeze-drying, to remove excess solvent from the compounds and thereby place the bioactive compounds in an appropriate form for storage or further use.

Yet a further aspect of the present invention provides a bioactive compound produced by a process as described herein. A further aspect provides a composition comprising a limonoid glycoside. The present invention may significantly enhance the purity of recovered of bioactive compounds from vegetable materials and vegetable extracts. The invention may also lead to increased recoveries of purified bioactive compounds. For example, limonoid glucosides are able to be recovered from citrus fruits at a concentration of about 50% to 70% on a dry weight basis. This compares favourably to processes of the prior art in which limonoid glucosides can typically be recovered in amounts which may be as low as about 10% to 15%. In addition, the process of the invention advantageously provides improved purity of the recovered bioactive compounds. Accordingly, polymethoxylated flavones can be recovered with less mixing with the bitter principle limonin.

Because bioactive compounds prepared in accordance with the process of the invention are of improved purity they are more easily formulated into functional foods allowing much smaller overall doses to provide an effective dose of the target bioactive and hence a reduced likelihood of undesirable flavours imparted in the food formulation.

EXAMPLES

The following examples illustrate the present invention in further detail however the examples should by no means be construed as limiting the scope of the invention as described herein.

Materials and Methods

Orange Peel Extract

Orange peel extract (OPE) was supplied as a 20.4 Brix solution by Lang Technologies. Brix was determined by measuring specific gravity and use of conversion tables. Briefly, the mass of 25 ml of OPE was measured on an electronic balance. The specific gravity was determined by dividing this mass by that of the same volume of de-ionized water and was found to be 1.085. From conversion tables, this is equivalent to 20.4 Brix. The pH of the OPE was about 4.0 (Merck Universal Indicator paper). FIG. 1 shows a HPLC chromatogram of a representative sample of orange peel extract.

Alcohol

Alcohol used in the eluting solvents was supplied as undenatured 95% ethanol.

High Performance Liquid Chromatography (HPLC)

HPLC was used to monitor the progress of the elution of bioactive compounds from the adsorbent polymer resins. HPLC was performed under the following conditions:

Apparatus: Shimadzu VP7 HPLC system consisting of low-pressure mixing system, SPD-M10A VP diode array detector and VP software to control gradient and detector.

Mobile Phase D: 0.1% (v/v) Aqueous Phosphoric Acid.

Mobile Phase A: Acetonitrile

Run Time 55 minutes

Column: Alltima C1 8 5 u Part Number 88056 with guard column

Monitoring Wavelength 210 and 280 nm (data collected between 200 nm and 350 nm in 2 nm steps).

Oven Temperature: 30° C.

Flow Rate: 1.0 ml/min (back pressure 2915 kgf/cm$^2$).

Injection Volume 20 μl

The HPLC gradient used to determine the presence of limonoid compounds is shown in Table 1.

TABLE 1

HPLC Gradient used to determine limonoid glycosides.

| Time (minutes) | Solvent D Conc. |
|---|---|
| 0.01 | 90.0% |
| 35.00 | 70.0% |
| 45.00 | 60.0% |
| 46.00 | 90.0% |
| 55.00 | Stop |

Column back pressure was monitored from run to run to ensure that performance was the same.

Example 1

Separation of Bioactive Compound with Acrylic Polymer Adsorbent

A glass column internal diameter 40 mm and height 540 mm fitted with a Teflon tap was partially filled to a height of 350 mm with an ethylene glycol crosslinked polymethylmethacrylate absorbent polymer resin in non-ionic form (CAS 25777-18-5) (supplied as Alimentech P495 Inert Absorbent Polymer by Bucher Foodtech). The resin bed volume was 400 ml with an interstitial dead volume of 180 ml. The acrylic polymer adsorbent was conditioned by washing with ten bed-volumes of water prior to use.

Three 250 ml aliquots of OPE (750 ml OPE in total) were applied to the top of the column containing the acrylic polymer adsorbent, with each aliquot allowed to percolate down the column at a rate of 4 ml/minute. At this rate each aliquot took about an hour to elute through the column. After application of the OPE, the column was washed with two 250 ml aliquots of water.

An eluting solvent containing a mixture of alcohol and water was then applied to the top of the column in 250 ml aliquots. The concentration of alcohol in the eluting solvent increased with each aliquot applied. The eluting solvent passed through the column and was subsequently collected in fractions and analysed by HPLC.

It is noted that the alcoholic strength of the eluted fractions may be somewhat less than that applied to the top of the column as the latter admixes with the liquid remaining within the interstitial "dead volume" of the polymer adsorbent. It is estimated that the concentration of alcohol is lower by approximately one third of the difference between the strength of the current eluate fraction and the prior one it is replacing. Thus, for example, if a 20% solution was added after a 10% solution, the concentration of alcohol in the eluate would be around 17%.

A total of twelve fractions were collected for analysis by HPLC. Their descriptions appear in Table 2.

TABLE 2

| Fraction | Identity |
|---|---|
| 1 | Eluate after First 250 mL OPE applied |
| 2 | Eluate after Second 250 mL OPE applied |
| 3 | Eluate after Third 250 mL OPE applied |
| 4 | First Water Wash |
| 5 | Second Water Wash |
| 6 | 10% Ethanol in water |
| 7 | 20% Ethanol in water |
| 8 | 30% Ethanol in water |
| 9 | 40% Ethanol in water |
| 10 | 50% Ethanol in water |
| 11 | 60% Ethanol in water |
| 12 | 80% Ethanol in water |

Results

Chromatograms corresponding to the results of HPLC analysis of the above fractions are shown in FIGS. 2 to 6. The components of the OPE were identified by retention time. The Figures show that a variety of components are present in the fractions leaving the column.

Figure 2:
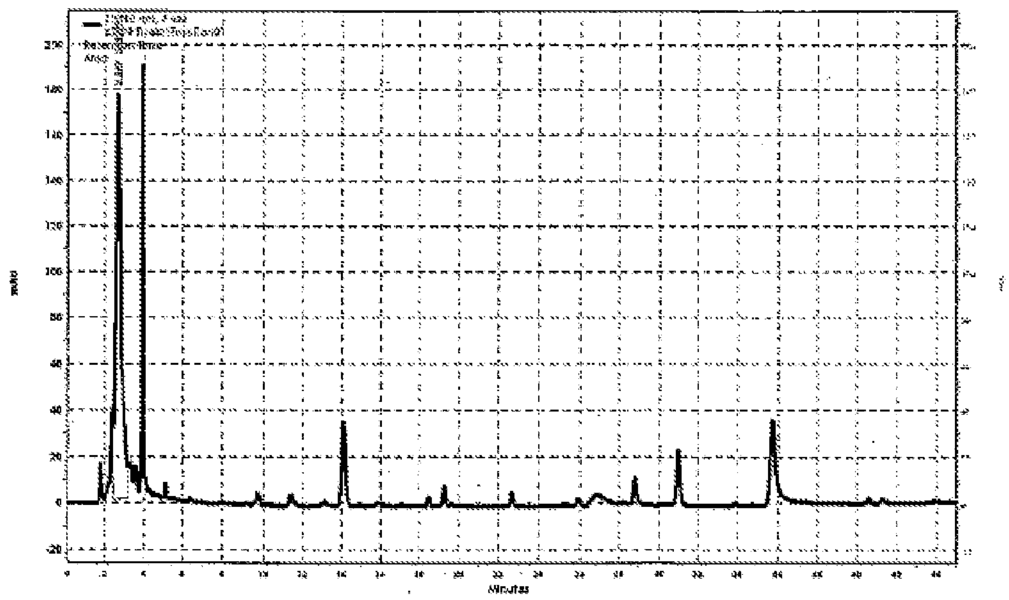
FIG. 2 shows a HPLC chromatogram illustrating the presence of sugars and organic acid compounds in a fraction of an eluate collected after the orange peel extract is passed over an acrylic polymer adsorbent in accordance with one embodiment of the invention.

The chromatogram obtained from fraction 1 is shown in FIG. 2. As seen in FIG. 2, the peaks are small, with most material eluting within four minutes. The first peak at 2 minutes corresponds to sugars, and the second at 4 minutes is phlorin, a major constituent of orange peel extract. Similar results were also obtained for fractions 2 to 6.

Figure 3:
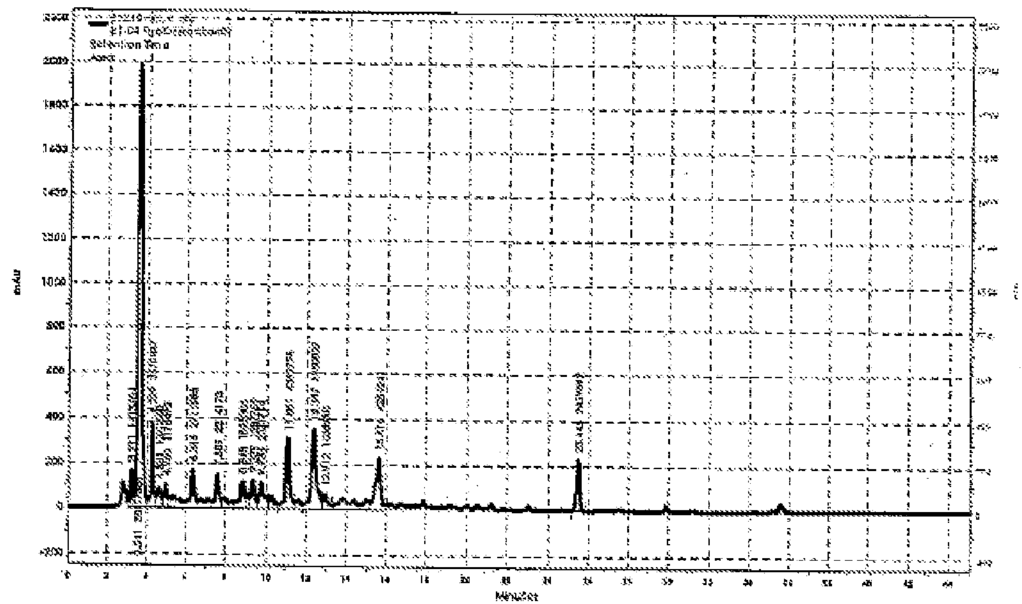
FIG. 3 shows a HPLC chromatogram illustrating the presence of limonin glucoside (LG) in a fraction of collected eluate.

In fraction 7, the peaks are starting to increase in size as shown in FIG. 3. The peak at 25.48 is limonin glucoside (LG).

In fractions 8 and 9, the peak corresponding to limonin glucoside was observed to increase. In addition, as seen in the chromatogram obtained for fraction 9 (FIG. 4), four peaks were observed with a typical limonoid conformance, namely limonin glucoside (25.39 minutes), a related limonoid (29.9 minutes), nomilin glucoside (NG) (34.16 minutes) and obacunone glucoside (OG) at 36.98 minutes.

In fraction 10, the limonoid at 34 minutes was observed to be still significant but those eluting earlier have decreased significantly in size.

Figure 5:
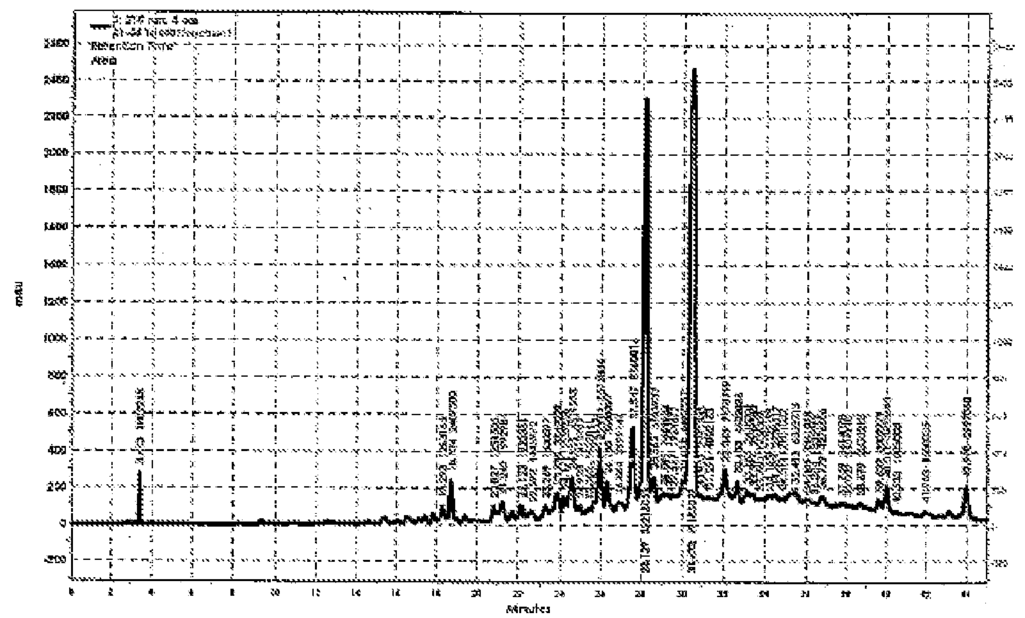
FIG. 5 shows a HPLC chromatogram illustrating the presence of flavonoids hesperidin and narirutin in a fraction of collected eluate.

As the alcohol concentration increases to around 60% in fraction 11, flavonoid compounds begin to elute as shown in FIG. 5. The two major peaks here are the flavonoids hesperidin (28.13 minutes) and narirutin (30.36 minutes).

Figure 6:
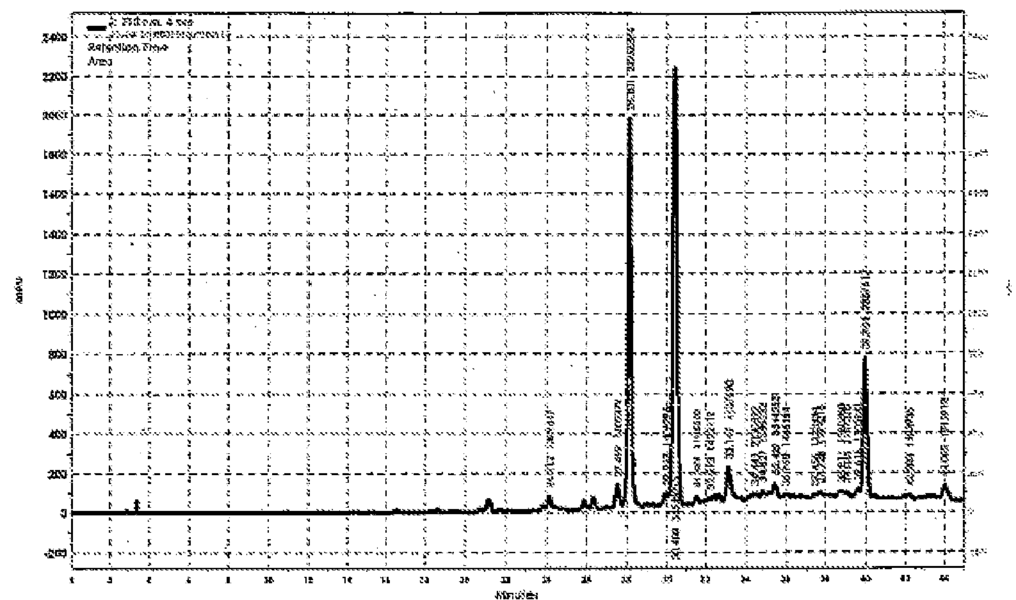
FIG. 6 shows a HPLC chromatogram illustrating the presence of flavonoids hesperidin, narirutin and neoponcirin in a fraction of collected eluate.

In fraction 12, the alcohol concentration is around 80%. As seen in FIG. 6, the predominant compounds in fraction 12 are hesperidin and narirutin with another flavonoid at 40.04 minutes considered to be neoponcirin (didymin).

Determination of Limonin Glucoside Concentration As commercial limonin glucoside standards are not available, the concentration of limonoid glucosides was determined against limonin (Sigma Aldrich) by comparison of peak areas and application of a conversion value (1.4) to allow for the molecular weight of glucose.

A linearity check of the HPLV system was carried out using limonin standards. The results of the linearity check and calibration are shown in Table 3.

TABLE 3

| Results of linearity check and calibration | |
|---|---|
| Concentration | Peak Area 210 nM |
| 150 | 9848525 |
| 300 | 19645424 |
| 450 | 2935005 |
| 600 | 3918728 |
| 750 | 4886204 |

A calibration chart of concentration vs peak area (at 210 nm) was constructed for limonin and used to determine the limonoid content of the collected fractions.

The raw data of limonoid content in fractions 7-10 is shown in Table 4 together with the limonoid content of a Comparative Example:

TABLE 4

| Raw Data (Area) | | | |
|---|---|---|---|
| | Peak Areas | | |
| Fraction | LG | NG | OG |
| 7 | 2459092 | 245909 | |
| 8 | 4427660 | 442766 | 1869183 |
| 9 | 7236151 | 1269381 | 2532814 |
| 10 | 2531755 | | |
| Comparative Example | 7022709 | ND | |

By comparison with the calibration chart, an estimate of the amount of limonoid glucoside in the orange peel extract may be obtained. The results are shown in Table 5.

TABLE 5

| Concentrations of LG's in OPE (ppm) | | | |
|---|---|---|---|
| Fraction | LG | NG | OG |
| 7 | 375 | 36 | |
| 8 | 679 | 66 | 286 |
| 9 | 1110 | 193 | 387 |
| 10 | 387 | | |
| Comparative Example | 1077 | | |

NG and OG were not determined in the original because of interferences due to other compounds.

As seen in this Example, the limonoids appear to be less strongly retained on the acrylic polymer resin and eluted from the acrylic resin at a lower alcohol concentration than the flavonoid compounds. This allowed the limonoid compounds to be separated from the flavonoid compounds without significant cross-contamination of the collected fractions.

Example 2

Separation of Bioactive Compound with Anion Exchange Resin Column

A column of 2 cm diameter and 20 cm in length was filled to a height of 200 mm with a weak anion exchange resin (Diaion WA-30 resin average particle size 0.47 mm, total exchange capacity 1.5 meq/mL supplied by Supelco). The resin bed volume was 50 mL. The anion exchange resin (WA-30) was conditioned prior to use by washing with 2 bed-volumes (100 mL) of 0.5M sodium hydroxide, followed by five bed volumes (250 mL) of water, followed by 2 bed volumes of 0.5M hydrochloric acid, followed by five bed volumes of water. The pH of the final washing water was 4.2.

Fractions 8 and 9 from Example 1 were treated to further purify the limonoid glucosides in these fractions. These fractions, which 30 and 40% alcohol respectively, conveniently contain a high proportion of LG's.

Fraction 8 was poured on to the top of conditioned weak anion exchange (WA-30) resin. The solution was allowed to pass through the column and the eluate was collected and analysed by HPLC.

In a similar manner, fraction 9 was poured on to the top of the WA-30 resin and the eluate was similarly collected and analysed by HPLC.

The anion exchange resin was then subsequently washed with 250 ml of 30% alcohol. Three 150 mL aliquots of 0.5M NaCl were then passed through the anion exchange resin and fractions of the eluted salt solution were collected and analysed by HPLC.

Results

Table 6 lists each of the analyses undertaken by HPLC.

TABLE 6

HPLC Gradient used to

| Time | Solvent D Conc. |
|---|---|
| 0.01 | 90.0 |
| 35.00 | 70.0 |
| 45.00 | 60.0 |
| 46 | 90.0 |
| 55.00 | Stop |

Figure 4:
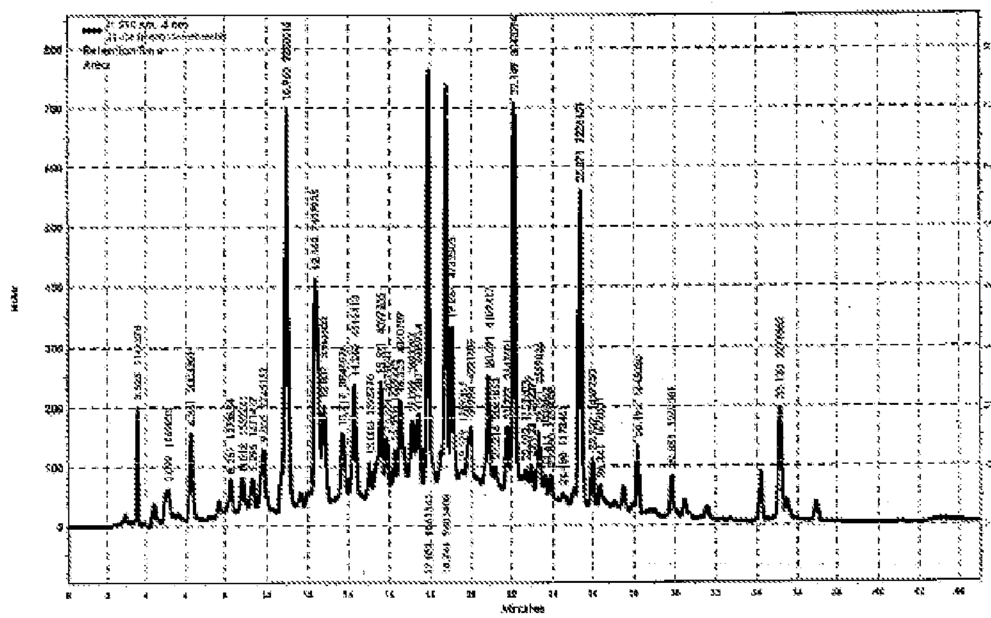
FIG. 4 shows a HPLC chromatogram illustrating the presence of limonin glucoside, a related limonoid, nomilin glucoside and obacunone glucoside in a fraction of collected eluate.
Figures 7, 8:
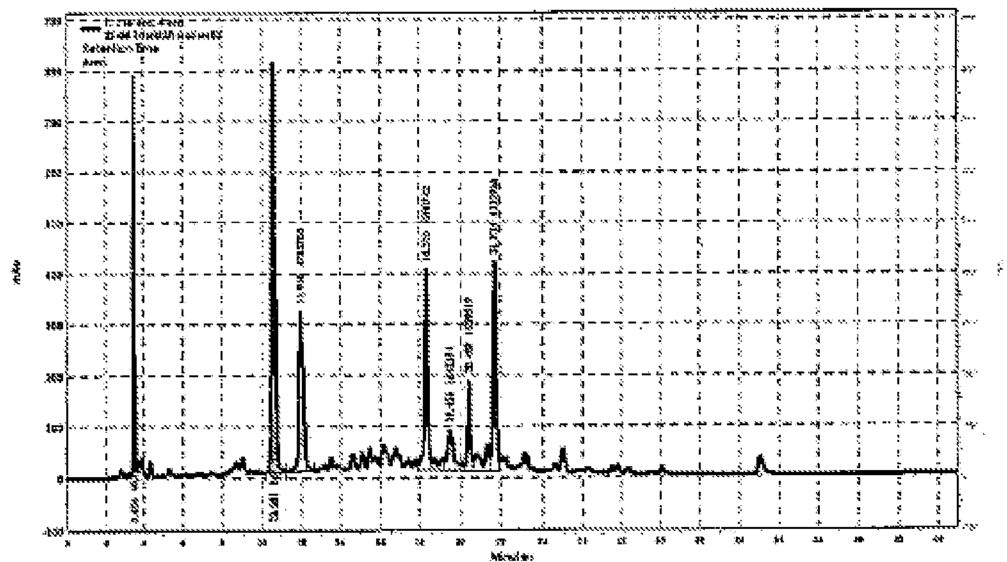
FIG. 7 shows a HPLC chromatogram illustrating the absence of limonoid glucosides in a fraction of an eluate collected after a solution containing limonoid glucosides has passed over an anion exchange resin in accordance with another embodiment of the invention.
FIG. 8 shows a HPLC chromatogram illustrating the presence of limonoid glucosides in an eluate fraction collected after a salt solution has been used to displace the limonoid glucosides from an anion exchange resin.

A chromatogram of the eluate obtained after application of fraction 9 on to the WA-30 column is shown in FIG. 7. The peaks corresponding to the limonoids in fraction 9, which were previously observed in FIG. 4, are absent because the WA-30 resin has retained these compounds. Other components have not been retained by the resin and have eluted from the column. A similar result was observed after fraction 8 was applied to the WA-30 resin. This shows that the limonoid compounds are bound to the WA-30 resin.

The passage of aliquots of 0.5M NaCl over the WA-30 resin was used to desorb the limonoid compounds from the resin. A chromatogram of an eluate obtained after passing 300 ml of 0.5M NaCl over the WA-30 resin is shown in FIG. 8. As seen in FIG. 8, the eluate fraction is rich in LG's. LG's do not have a UV extinction coefficient as high as the flavonoids, so the purity of LG's in this fraction appears to be greater than 75%.

This result shows that limonoid glucosides can be purified by selectively adsorbing the LG's on to an ion exchange resin. A salt solution is then able to effectively remove the bound limonoid glucosides from the resin. The resultant purified limonoid glucosides appear to have a purity in excess of 50%. In addition, the purified limonoid glucosides are not contaminated by sugars, or flavonoids such as narirutin, hesperidin and neoponcirin.

Example 3

Process for Recovering Bioactive Compounds from Orange Peel Extract (OPE)

A process for separating bioactive compounds from orange peel extract (OPE) is described. The process used four separate columns as follows:

Column A: The column was glass with internal diameter 40 mm and height 540 mm fitted with a Teflon tap. It was partially filled to a height of 200 mm with acrylic resin (Alimentech P495 Inert Absorbent Polymer supplied by Bucher Foodtech). The resin bed volume was 250 mL and the interstitial dead volume was 110 mL.

Column B: The column was glass with internal diameter 23 mm and height 180 mm fitted with a Teflon tap. It was partially filled to a height of 180 mm with polystyrene-divinylbenzene resin (Amberlite XAD-16 Surface Area 800 $m^2/g$, Average Pore Diameter 100 Angstroms supplied by Sigma-Aldrich). The resin bed volume was 50 mL.

Column C: The column was glass with internal diameter 23 mm and height 180 mm fitted with a Teflon tap. It was partially filled to a height of 200 mm with a weak anion exchange resin (Diaion WA-30 resin average particle size 0.47mm, total exchange capacity 1.5 meq/mL supplied by Supelco). The resin bed volume was 50 mL.

Column D: The column was glass with internal diameter 23 mm and height 180 mm fitted with a Teflon tap. It was partially filled to a height of 180 mm with resin (Amberlite XAD-16 Surface Area 800 $m^2/g$, Average Pore Diameter 100 Angstroms supplied by Sigma-Aldrich). The resin bed volume was 50 mL.

The OPE and polymer adsorbent resins were used as supplied or were prepared prior to use in accordance with the general procedures described above.

The elution of bioactive compounds from each column was monitored by High Performance Liquid Chromatography (Shimadzu VP7 HPLC system consisting of low-pressure mixing system FCV-10AL, degassing system DGU-14A, solvent delivery module LC-10AD, autosampler SIL-10AD, diode array detector SPD-M10A VP and VP software.)

Column A (Acrylic Polymer Adsorbent):

The acrylic polymer adsorbent was shown in this experiment to separate limonoid glucosides from flavonoid compounds.

Six litres of 4.1 Brix OPE were loaded onto the column containing the acrylic polymer adsorbent (column A) in 1 litre aliquots. The OPE was allowed to percolate through the column after the application of each aliquot.

Initially, after 1 litre of the OPE had passed through the column, no limonoid or flavonoid compounds are eluted from the column. After 2 litres of OPE had been applied to the column, limonoid compounds (principally limonin glucoside at retention time 19 minutes) were observed to elute from the column. After a total of 3, 4 and 5 litres of OPE had been applied to the acrylic resin, more limonoid compounds, principally limonin glucoside (LG), deacetyl nomilin glucoside (DANG) (retention time 24.5 minutes), nomilin glucoside (NG) (retention time 28.4 minutes) and nomilic acid glucoside (NAG) (retention time 29 minutes) were observed to be eluted from the acrylic resin. After 6 litres of OPE had been applied to the column, obacunone glucoside (OG) (retention time 31 minutes) was observed to be eluted from the column in addition to the limonoid compounds identified previously.

Figure 9:
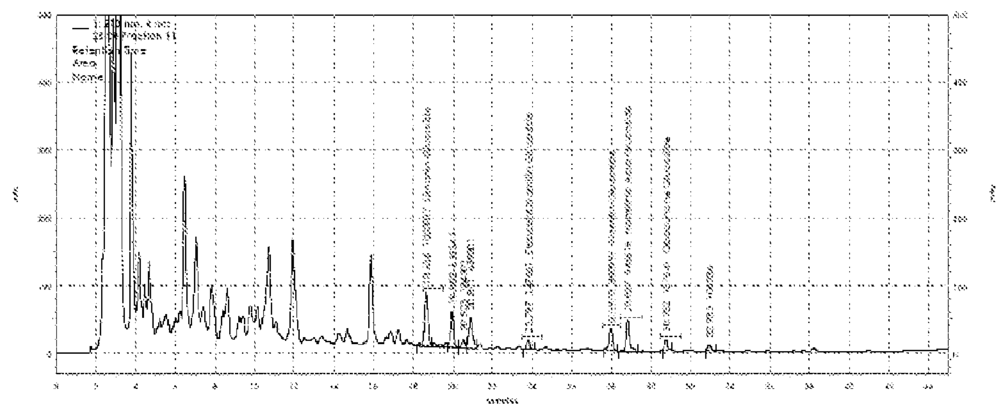
FIG. 9 shows a HPLC chromatogram illustrating the presence of limonoid glucosides in a fraction of orange peel extract (OPE) eluted from an acrylic polymer adsorbent (column A) in a process in accordance with one embodiment of the invention.
Figure 10:
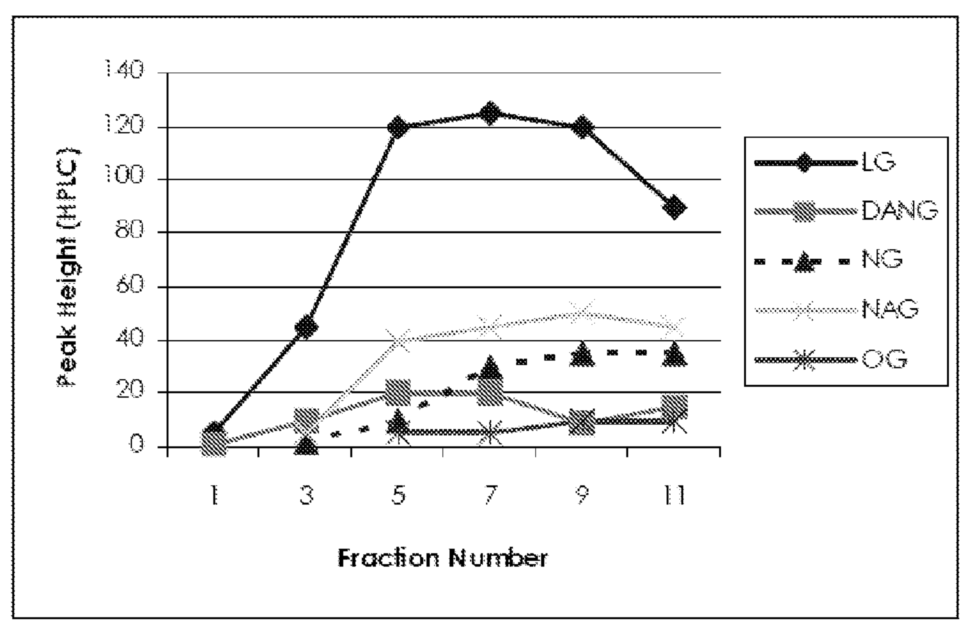
FIG. 10 shows a graph illustrating the relative amounts of different limonoid glucosides obtained in various fractions of OPE eluted from the acrylic polymer adsorbent (column A) in a process in accordance with one embodiment of the invention.

A HPLC chromatogram of the eluate obtained after 6 litres of OPE has eluted through Column (A) is shown in FIG. 9. The relative amounts of each limonoid glucoside compound eluted from the acrylic polymer resin may be determined and a graph illustrating the relative amounts of each limonoid glucoside compound is shown in FIG. 10.

In none of the collected eluates was the presence of any of the major flavonoid compounds detected. Consequently, it is shown that the acrylic polymer adsorbent was able to substantially remove the flavonoid compounds from the OPE while the limonoid compounds, which were not adsorbed on to the acrylic resin, were allowed to pass through.

As discussed below, the OPE fractions eluted from Column (A) may then be loaded onto Column (B) to purify the limonoid glucosides and to also prepare a palatable "juice" from the natural sugars and other highly polar compounds present in the OPE.

Once the OPE had been allowed to pass through the acrylic resin, the column was then washed with two bed volumes of water. Further quantities of limonoid compounds were eluted from the column with the water however no flavonoid compounds were observed to be present in the water eluate.

An aqueous ethanol eluent solution was then applied to the top of the column to elute the flavonoid compounds that had been adsorbed on to the acrylic polymer resin. A gradient alcohol concentration that increased in a step-wise manner from 20% (v/v) to 60% (v/v) was applied in accordance with Table 7. After application, each aliquot of eluent was allowed to percolate through the column to desorb the bioactive flavonoid compounds from the acrylic resin. The desorbed compounds were subsequently collected and analysed by HPLC.

TABLE 7

| Fraction | Strength (% Ethanol) | Bed Volumes |
|---|---|---|
| 15 | 20 | 1 |
| 16 | 30 | 1 |
| 17 | 40 | 1 |
| 18 | 50 | 1 |
| 19 | 60 | 1 |
| 20 | 80 | 1 |

The eluate obtained after desorbing the acrylic resin (column (A)) with a solution containing 20% ethanol did not contain any flavonoid compounds. However, when the concentration of ethanol in the eluent was increased to 30%, the resulting eluate did contain a small amount of flavonoids. Further increasing the ethanol concentration in the eluate to 40% and 50% resulted in significant amounts of flavonoid compounds narirutin (retention time 22 minutes) and hesperidin (retention time 24.35 minutes) being desorbed and eluted from the acrylic resin. When the amount of ethanol in the eluent was increased to 60%, the resulting eluate contained a significant amount of narirutin and hesperidin as well as didymin at a retention time of 27 minutes.

Figure 11:
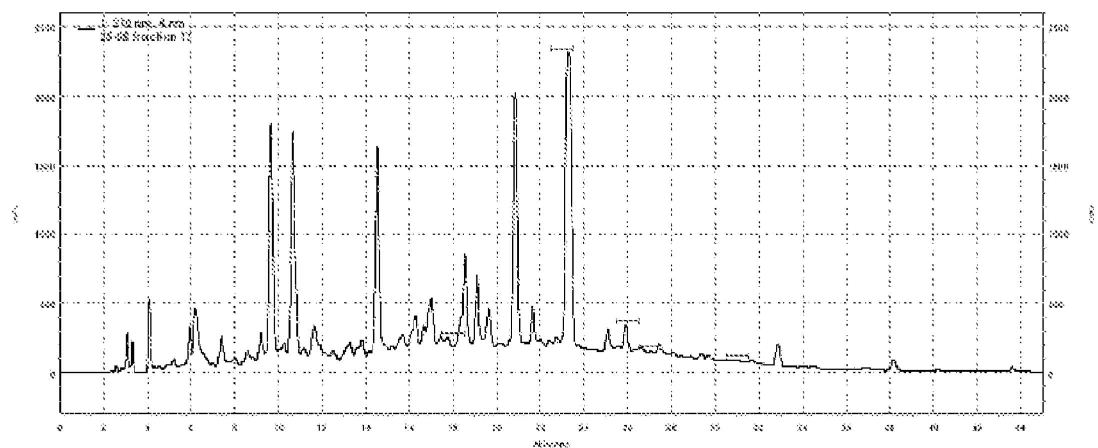
FIG. 11 shows a HPLC chromatogram illustrating the presence of flavonoids in an eluate fraction collected after elution of the acrylic polymer adsorbent (column A) with 40% ethanol in a process in accordance with one embodiment of the invention.
Figure 12:
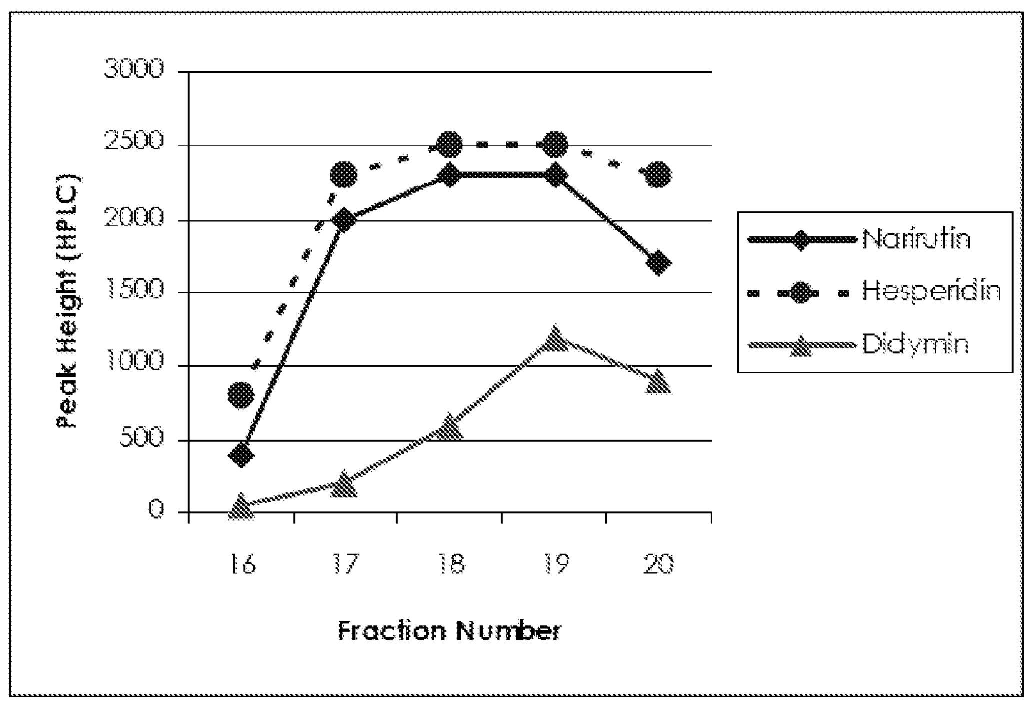
FIG. 12 shows a graph illustrating the relative amounts of different flavonoid compounds in various eluate fractions obtained after desorption from the acrylic polymer adsorbent (column A) in a process in accordance with one embodiment of the invention.

A HPLC chromatogram of an eluate fraction obtained after desorption of the flavonoid compounds from column (A) with 40% ethanol is shown in FIG. 11. The relative amounts of each flavonoid compound desorbed from the acrylic polymer resin by each eluent fraction may be determined and a graph illustrating the relative quantities of flavonoid compounds collected as the alcohol concentration increased is shown in FIG. 12.

It has been found that the acrylic polymer resin holds up the flavonoids, but allows the limonoid glucosides to pass through along with more polar polyphenolics, sugars and organic acids. The flavonoids could then be desorbed from the acrylic resin using aqueous ethanol.

Column B (Polystyrene-Divinyl Benzene Adsorbent):

The polystyrene-divinylbenzene column is shown in the experiment to be useful in the separation of the limonoid glucosides from the natural sugars and more polar compounds eluting from Column (A).

In this trial, a total of six litres of 4.1 Brix OPE from Column (A) were loaded onto Column (B) containing the polystyrene-divinyl benzene polymer absorbent, in 1 L aliquots as they came off the acrylic resin column. The OPE aliquots were allowed to percolate through the polystyrene-divinyl benzene resin and the eluted aliquots were collected and analysed by HPLC.

Figure 13:
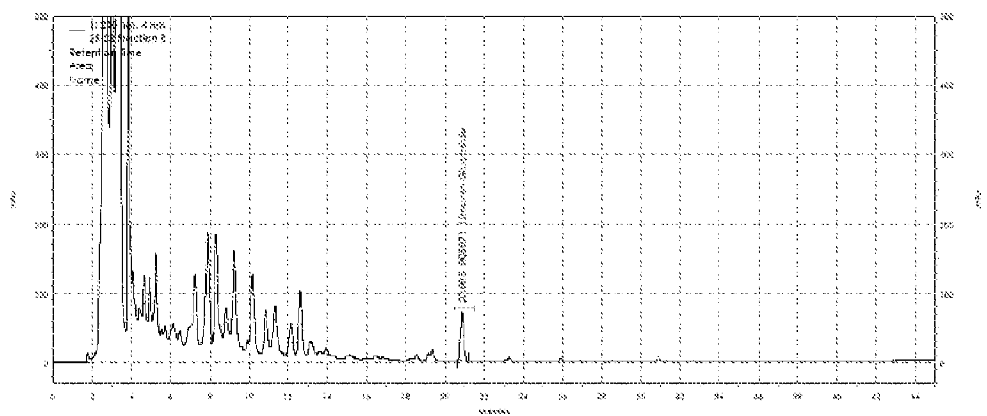
FIG. 13 shows a HPLC chromatogram illustrating the absence of flavonoids and limonoid glucosides in the residual juice fraction obtained after elution of an OPE fraction from a polystyrene-divinyl benzene polymer adsorbent (column B) in a process in accordance with one embodiment of the invention.

After application of the first two aliquots of OPE onto Column (B), no limonoid glucosides were observed to be eluted from the column. After application and elution of the third and fourth aliquots of OPE, a small amount of limonoid glucosides (but no flavonoid compounds) was observed to pass through the column. After application of the fifth and sixth aliquots of OPE on to Column (B), some limonin glucoside and small amounts of other limonid glucosides eluted from the column. The column was then washed with four bed volumes of water to remove the natural sugars and other highly polar material from the column. The water fractions were collected and may be combined with the eluted OPE fractions to form a palatable "juice" component that is free of any bitter compounds A HPLC chromatogram of the "juice" component obtained from column (B) is shown in FIG. 13. The OPE eluates obtained from Column (B) did not have the major flavonoids (principally hesperidin, narirutin and didymin), nor did they contain the five limonoid glucosides, limonin glucoside, deacetyl nomilin glucoside, nomilin glucoside, nomilic acid glucoside and obacunone glucoside. The OPE eluate obtained from Column (B) contained polyphenolics plus sugars and organic acids. The eluate is suitable for blending back into food products such as orange juice, to supplement the food product.

The limonoid glucosides retained on Column (B) were then desorbed from the column with an aqueous ethanol eluent solution. As shown in Table 8, a stepped ethanol gradient that increased from 10% (v/v) to 80% (v/v) was used as the eluent.

TABLE 8

| Fraction | Strength (% Ethanol) | Bed Volumes |
|---|---|---|
| 21 | 10 | 2 |
| 22 | 20 | 2 |
| 23 | 30 | 2 |
| 24 | 50 | 2 |
| 25 | 80 | 2 |

After application, each aliquot of eluent was allowed to percolate through the column to desorb the limonoid glucoside compounds from Column (B) and were subsequently collected and analysed by HPLC.

It was observed that the eluate obtained after desorbing the polystyrene-divinyl benzene polymer resin (column B) with a solution containing 10% ethanol contained some limonoid glucosides, principally deacetyl nomilin glucoside (retention time 25 minutes) and nomilin glucoside (retention time 29 minutes).

Upon increasing the concentration of alcohol in the eluent to 20%, other limonoid glucoside compounds, limonin glucoside, nomilinic acid glucoside and obacunone glucoside were observed to elute from Column (B). Further increases in he concentration of ethanol in the eluent to 30%, 50% and 80% resulted in greater quantities of the five limonoid glucosides being desorbed from the polystyrene-divinyl benzene polymer resin.

Figure 14:
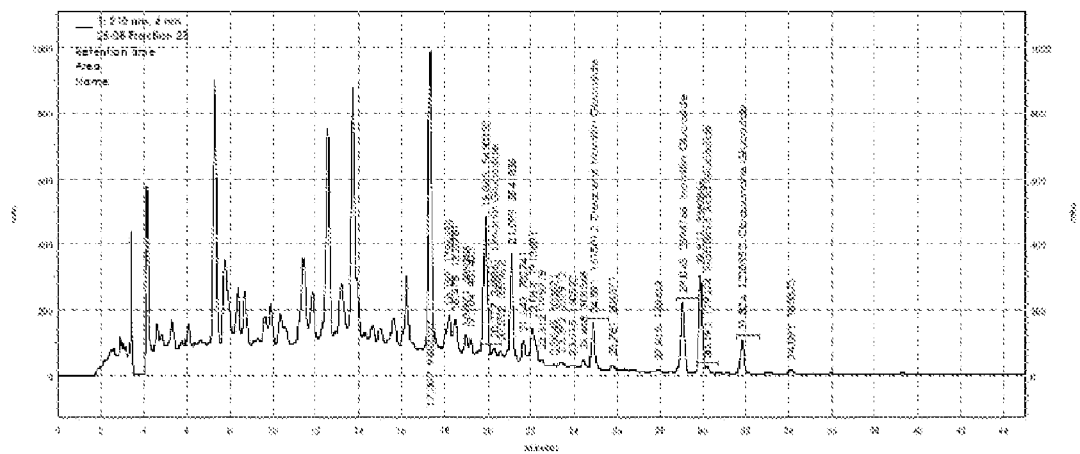
FIG. 14 shows a HPLC chromatogram illustrating the presence of limonoid glucoside compounds in an eluate fraction collected after elution of the polystyrene-divinyl benzene polymer adsorbent (column B) with 30% ethanol in a process in accordance with one embodiment of the invention.
Figure 15:
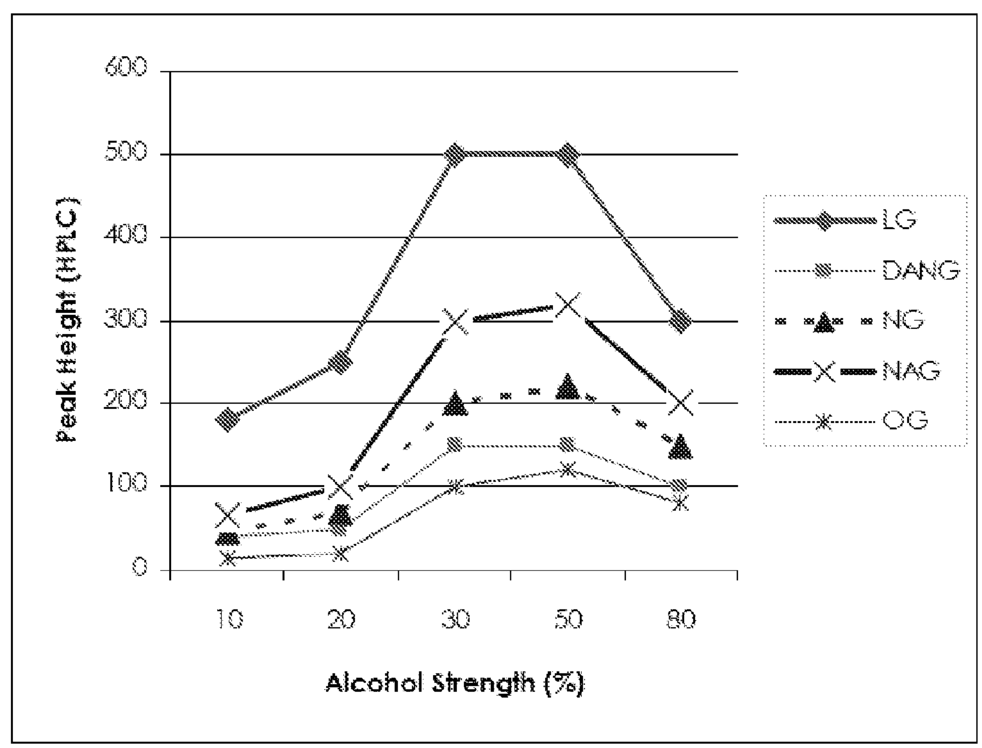
FIG. 15 shows a graph illustrating the relative amounts of different limonoid glucoside compounds in various eluate fractions obtained after desorption from the polystyrene-divinyl benzene polymer adsorbent (column B) in a process in accordance with one embodiment of the invention.

A HPLC chromatogram of an eluate fraction obtained after desorption of the limonoid glucoside compounds from column (B) is shown in FIG. 14. The relative amounts of each limonoid glucoside compound desorbed from the polystyrene-divinyl benzene polymer resin in each eluate fraction may be determined and a graph illustrating the relative quantities of each limonoid glucoside collected is shown in FIG. 15.

Column C (Weak Anion Exchange Resin):

The weak anion exchange column is shown in this experiment to be useful in the separation of the limonoid glucosides from the more neutral compounds eluting from Column (B).

The eluates containing the limonoid glucosides desorbed from Column (B) were combined and diluted with water to a strength of around 20% ethanol by volume. The combined eluates were then applied to the top of Column (C) and allowed to percolate through the column at a rate of about ten bed volumes per hour. The liquid passing through the column was discarded. However, it is envisaged that in a commercial application, the liquid could be diverted and the alcohol subsequently recovered. HPLC analysis showed that the liquid which passed through column (C) did not contain any limonoid glucosides.

Figure 16:
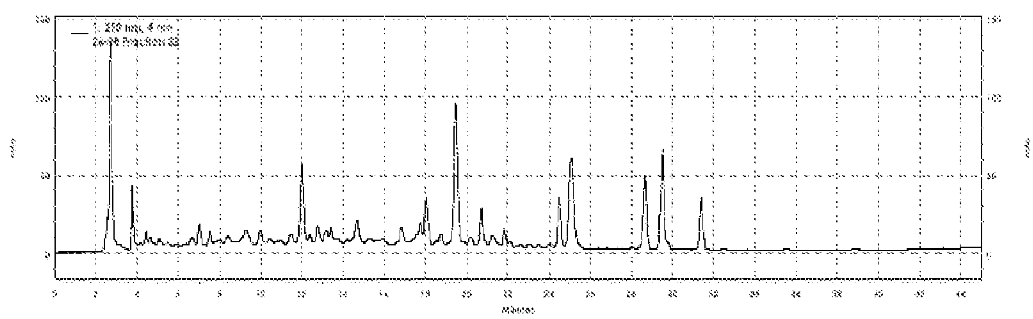
FIG. 16 shows a HPLC chromatogram illustrating the presence of limonoid glucoside in an eluate collected after elution of a weak anion exchange resin (column C) with 0.5M sodium chloride in a process in accordance with one embodiment of the invention.
Figure 17:
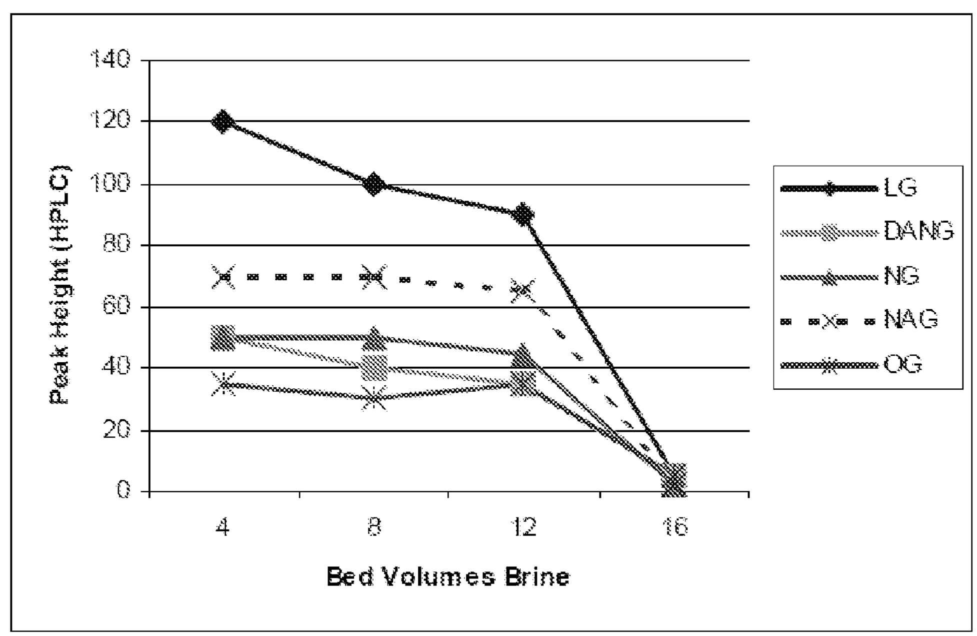
FIG. 17 shows a graph illustrating the relative amounts of different limonoid glucoside compounds in various eluate fractions obtained after desorption from the weak anion exchange resin (column C) in a process in accordance with one embodiment of the invention.

The limonoid glucosides were then desorbed from column (C) using a solution of 0.5M sodium chloride (brine) solution. Almost 100% of the limonoid glucosides had eluted within eight bed volumes of brine passing through the column. A HPLC chromatogram of the eluate obtained after passing a brine solution through the anion exchange resin of column (C) is shown in FIG. 16. A graph illustrating the amount of each limonoid glucoside desorbed from the anion exchange resin as increasing quantities of brine is applied to the resin is shown in FIG. 17.

Column D (Polystyrene-Divinyl Benzene Adsorbent):

The polystyrene-divinylbenzene polymer adsorbent was shown in this experiment to be useful in removing the sodium chloride salt from the limonoid glucoside compounds eluting from Column (C). The salt was observed to pass through the polystyrene-divinyl benzene polymer adsorbent of column (D) while the limonoid glucosides were retained by the polymer.

The brine solution containing the desorbed limonoid glucoside compounds obtained from column (C) is applied to the top of the polystyrene-divinyl benzene resin of column (D) and allowed to percolate through the polymer resin. The limonoid glucosides were observed to adsorb on to the polymer adsorbent while the sodium chloride in the brine does not. Column (D) was then washed with four bed volumes of water to remove the sodium chloride salt.

Figure 18:
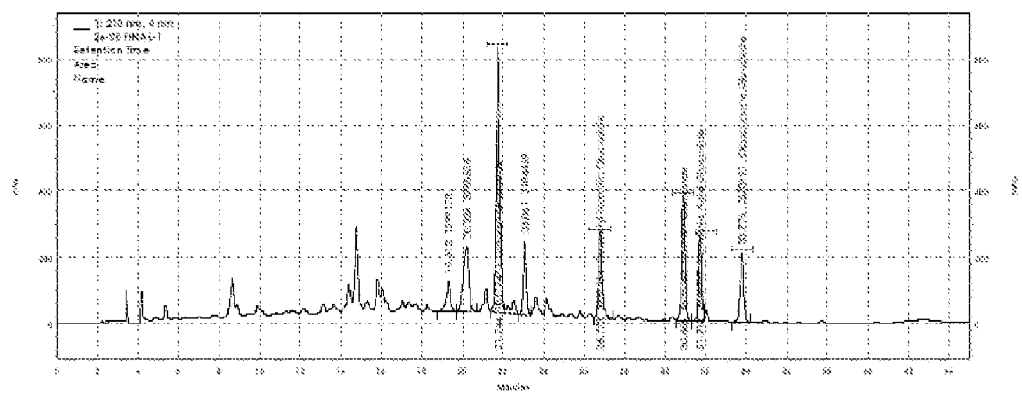
FIG. 18 shows a HPLC chromatogram illustrating the limonoid glucosides compounds in eluate fractions collected after elution of a polystyrene-divinyl benzene polymer adsorbent (column D) with 50% ethanol in a process in accordance with one embodiment of the invention.

The limonoid glucosides were then desorbed from the polystyrene-divinyl benzene polymer resin with an eluent solution containing 50% aqueous ethanol. The HPLC chromatogram of an eluate fraction collected after desorption of the limonoid glucosides is shown in FIG. 18.

Figure 19:
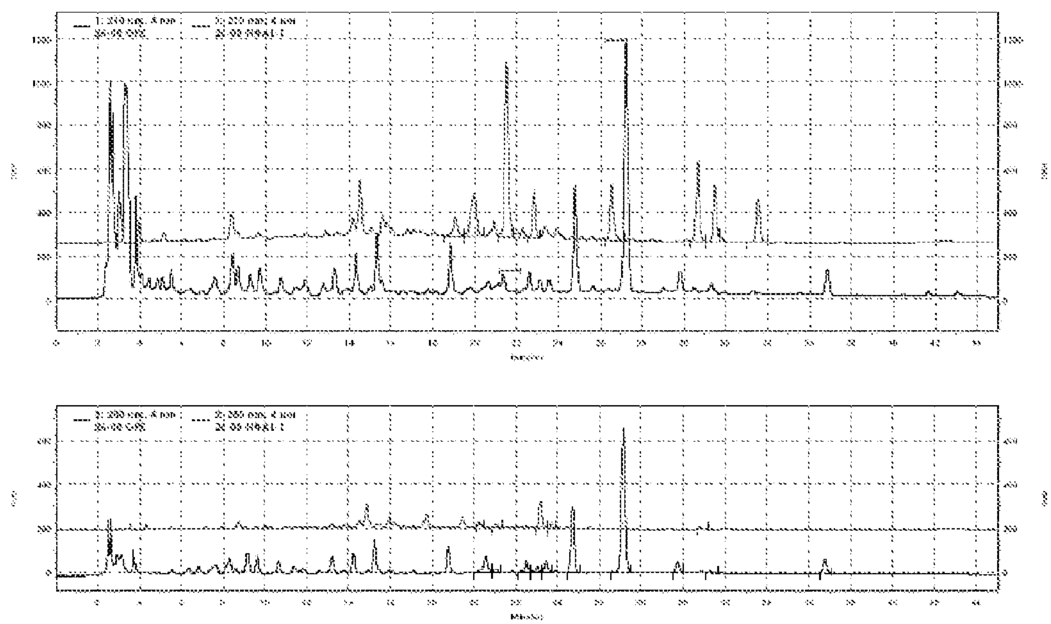
FIG. 19 shows stacked HPLC chromatograms illustrating the components in a raw orange peel extract (lower line in each chromatogram) and in a concentrated limonoid glucoside fraction (upper line in each chromatogram) obtained by a process in accordance with one embodiment of the invention.

An outcome of the process is that a concentrated limonoid glucoside fraction can be obtained. As seen in stacked HPLC chromatograms of FIG. 19 showing the original Orange Peel Extract (lower line in each chromatogram) and the concentrated limonoid glucoside fraction (upper line in each chromatogram), the concentration of LG's in the original OPE are about 1000 parts per million in total, and individual peaks are hard to see. In the resultant concentrated fraction however, the LG's amount to more than 80% of the components in the concentrate. Given that 12 Brix OPE contains 1000 ppm LG's in toto, every litre contains 100 mg of pure LG's. Hence the process can produce one gram of LG's per litre of acrylic resin for each cycle of the process.

The above example demonstrates that different polymer adsorbent resins can be used to separate and purify bioactive compounds from orange peel extract without significant losses of the target compounds.

It is understood that various other modifications and/or alterations may be made without departing from the spirit of the present invention as outlined herein.

The invention claimed is:

1. A process for the separation of bioactive compounds obtained from vegetable matter, the process comprising the steps of (a) contacting a plurality of bioactive compounds with a first polymer adsorbent under conditions allowing adsorption of at least one bioactive compound onto the first adsorbent while at least one bioactive compound is not adsorbed onto the first adsorbent;

(b) collecting a solution comprising the at least one bioactive compound which has not adsorbed onto the first adsorbent; and (c) contacting the solution obtained in step (b) with a second polymer adsorbent under conditions allowing adsorption of at least one bioactive compound contained in the solution obtained in step (b) onto the second adsorbent, wherein the first polymer adsorbent is an acrylic polymer, the second polymer adsorbent is a polystyrene-divinyl benzene polymer, the plurality of bioactive compounds includes a flavanone glycoside and a limonoid glucoside, the flavanone glycoside is adsorbed onto the acrylic polymer, the limonoid glucoside is not adsorbed onto the acrylic polymer, and the limonoid glucoside is adsorbed onto the polystyrene-divinyl benzene polymer, thereby substantially separating the flavanone glycoside from the limonoid glucoside.

2. The process according to claim 1, wherein the first polymer adsorbent is an acrylic ester.

3. The process according to claim 2, wherein the first polymer adsorbent is polymethylmethacrylate.

4. The process according to claim 1, wherein the first polymer adsorbent and the second polymer adsorbent are each arranged in a column.

5. The process according to claim 1, further comprising, after step (a), the steps of:

contacting the at least one bioactive compound adsorbed on the first polymer adsorbent with an eluent under conditions allowing desorption of the at least one bioactive compound from the first polymer adsorbent; and eluting the at least one bioactive compound from the first polymer adsorbent.

6. The process according to claim 5, wherein the eluent comprises alcohol and water.

7. The process according to claim 6, wherein the concentration of alcohol in the eluent remains substantially constant during desorption of the at least one bioactive compound from the first polymer adsorbent.

8. The process according to claim 6, wherein the concentration of alcohol in the eluent increases during desorption of the at least one bioactive compound from the first polymer adsorbent.

9. The process according to claim 1, further comprising, after step (c), the steps of:

contacting the at least one bioactive compound adsorbed on the second polymer adsorbent with an eluent under conditions allowing desorption of the at least one bioactive compound from the second polymer adsorbent; and eluting the at least one bioactive compound from the second polymer adsorbent.

10. The process according to claim 9, wherein the eluent comprises alcohol and water.

11. The process according to claim 10, wherein the concentration of alcohol in the eluent remains substantially constant during desorption of the at least one bioactive compound from the second polymer adsorbent.

12. The process according to claim 10, wherein the concentration of alcohol in the eluent increases during desorption of the at least one bioactive compound from the second polymer adsorbent.

13. The process according to claim 9, further comprising, after the eluting step, the step of:

contacting the at least one bioactive compound eluted from the second polymer adsorbent with an ion exchange resin under conditions allowing ionic interactions between the at least one bioactive compound and the resin such that the at least one bioactive compound is adsorbed onto the resin.

14. The process according to claim 13, wherein the ion exchange resin is an anion exchange resin.

15. The process according to claim 14, wherein the ion exchange resin is a weak base anion exchange resin.

16. The process according to claim 13, wherein the ion exchange resin is arranged in a column.

17. The process according to claim 13, further comprising, after the at least one bioactive compound is adsorbed on the ion exchange resin, the steps of:

contacting the at least one bioactive compound adsorbed on the ion exchange resin with a solution comprising a solute under conditions allowing the solute to displace the at least one bioactive compound from the resin; and eluting the at least one bioactive compound from the resin.

18. The process according to claim 17, wherein the solute is a salt.

19. The process according to claim 18, wherein the salt is sodium chloride.

20. The process according to claim 1, wherein the plurality of bioactive compounds are obtained from a citrus fruit.

21. The process according to claim 17, further comprising, after eluting the at least one bioactive compound from the ion exchange resin, the steps of:

contacting the at least one bioactive compound eluted from the ion exchange resin with a polymer adsorbent under conditions allowing adsorption of the at least one bioactive compound to the polymer adsorbent; and collecting the at least one bioactive compound from the polymer adsorbent.

22. The process according to claim 21, wherein the polymer adsorbent is polystyrene-divinyl benzene.

23. The process according to claim 21, wherein the at least one bioactive compound is collected from the polymer adsorbent by contacting the at least one bioactive compound adsorbed on the polymer adsorbent with an eluent under conditions allowing desorption of the at least one bioactive compound from the polymer adsorbent and eluting the at least one bioactive compound from the polymer adsorbent.

24. The process according to claim 23 wherein the eluent comprises alcohol and water.

* * * * *